US011813352B2

(12) United States Patent
Gu et al.

(10) Patent No.: US 11,813,352 B2

(45) Date of Patent: Nov. 14, 2023

(54) CHARGE-SWITCHABLE POLYMERIC DEPOT FOR GLUCOSE-TRIGGERED INSULIN DELIVERY WITH ULTRAFAST RESPONSE

(71) Applicant: North Carolina State University, Raleigh, NC (US)

(72) Inventors: Zhen Gu, Los Angeles, CA (US); Jinqiang Wang, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 322 days.

(21) Appl. No.: 16/765,064

(22) PCT Filed: Nov. 20, 2018

(86) PCT No.: PCT/US2018/061953

§ 371 (c)(1),
(2) Date: May 18, 2020

(87) PCT Pub. No.: WO2019/104006

PCT Pub. Date: May 31, 2019

(65) Prior Publication Data

US 2020/0360269 A1 Nov. 19, 2020

Related U.S. Application Data

(60) Provisional application No. 62/589,091, filed on Nov. 21, 2017.

(51) Int. Cl.

| | |
|---|---|
| ***A61K 9/00*** | (2006.01) |
| ***A61K 47/58*** | (2017.01) |
| ***A61P 3/10*** | (2006.01) |
| ***A61K 9/50*** | (2006.01) |
| ***A61K 9/51*** | (2006.01) |
| ***A61K 38/28*** | (2006.01) |

(52) U.S. Cl.

CPC .......... *A61K 9/0021* (2013.01); *A61K 9/5026* (2013.01); *A61K 9/5138* (2013.01); *A61K 38/28* (2013.01); *A61K 47/58* (2017.08); *A61P 3/10* (2018.01)

(58) Field of Classification Search

None

See application file for complete search history.

(56) References Cited

U.S. PATENT DOCUMENTS

| | | | |
|---|---|---|---|
| 8,137,697 | B1 | 3/2012 | Sung et al. |
| 2013/0034602 | A1 | 2/2013 | Qian et al. |
| 2016/0067190 | A1 | 3/2016 | Anderson et al. |

FOREIGN PATENT DOCUMENTS

| | | | |
|---|---|---|---|
| CN | 101273961 | * | 10/2008 |
| CN | 101273961 | A | 10/2008 |
| WO | WO 2016/172320 | A1 | 10/2016 |
| WO | WO 2019/104006 | A1 | 5/2019 |

OTHER PUBLICATIONS

Chou et al. (Glucose responsive insulin activity by covalent modification with aliphatic phenylboronic acid conjugates, PNAS, vol. 112, No. 8, Feb. 24, 2015). (Year: 2015).*

International Preliminary Report on Patentability Corresponding to International Application No. PCT/US 2018/061953 dated May 26, 2020.

International Search Report and Written Opinion of the International Searching Authority Corresponding to International Application No. PCT/US 2018/061953 dated Apr. 26, 2019.

European Search Report Corresponding to Application No. 18882215.9-1118 dated Oct. 6, 2021.

Kim et al., "Swelling Properties of Hydrogels Containing Phenylboronic Acids," Chemosensors, vol. 2, pp. 1-12 (2013).

Brooks et al., "Synthesis and Applications of Boronic Acid-Containing Polymers: From Materials to Medicine." Chem. Rev., vol. 116, pp. 1375-1397 (2016).

Brownlee et al., "Glycosylated Insulin Complexed to Concanavalin A: Biochemical Basis for a Closed-Loop Insulin Delivery System." Diabetes, vol. 32, pp. 499-504 (1983).

Brownlee et al., "A Glucose-Controlled Insulin-Delivery System: Semisynthetic Insulin Bound to Lectin." Science, vol. 206, pp. 1190-1191 (1979).

Chou et al., "Glucose-responsive insulin activity by covalent modification with aliphatic phenylboronic acid conjugates." Proc. Natl. Acad. Sci. USA, vol. 112, pp. 2401-2406 (2015).

The Diabetes Control and Complications Trial Research Group, "The Effect of Intensive Treatment of Diabetes on the Development and Progression of Long-Term Complications in Insulin-Dependent Diabetes Mellitus." N. Engl. J. Med., vol. 329, pp. 977-986 (1993).

Cresto et al., Acta Physiol. Lat. Am., vol. 27, pp. 7-15 (1977).

Di et al., "Stretch-Triggered Drug Delivery from Wearable Elastomer Films Containing Therapeutic Depots." ACS Nano, vol. 9, pp. 9407-9415 (2015).

Di et al., "Ultrasound-triggered noninvasive regulation of blood glucose levels using microgels integrated with insulin nanocapsules." Nano Res, vol. 10, pp. 1393-1402 (2017).

(Continued)

*Primary Examiner* — Melissa S Mercier

(74) *Attorney, Agent, or Firm* — Jenkins, Taylor & Hunt P.A.,

(57) ABSTRACT

A composition comprising a glucose-responsive charge-switchable polymer is described. In the absence of glucose or under normoglycemic conditions, the positively charged polymer can be complexed with negatively charged therapeutic agents, such as insulin. Under hyperglycemic conditions, the positive charge of the polymer is reduced, and the polymer/therapeutic agent complex can disassemble, allowing the therapeutic agent to be released. Pharmaceutical compositions, nanoparticles, and microneedle arrays of the polymer and/or polymer/therapeutic agent complex and methods of treating diabetes are also described.

30 Claims, 13 Drawing Sheets

(56) References Cited

OTHER PUBLICATIONS

Dong et al., "Injectable and Glucose-Responsive Hydrogels Based on Boronic Acid-Glucose Complexation." Langmuir, vol. 32, pp. 8743-8747 (2016).
Veregin et al., "Free radical polymerizations for narrow polydispersity resins: electron spin resonance studies of the kinetics and mechanism." Macromolecules vol. 26, pp. 5316-5320 (1993).
Gordijo et al., "Nanotechnology-Enabled Closed Loop Insulin Delivery Device: In Vitro and In Vivo Evaluation of Glucose-Regulated Insulin Release for Diabetes Control." Adv. Funct. Mater., vol. 21, pp. 73-82 (2011).
Gu et al., "Injectable Nano-Network for Glucose-Mediated Insulin Delivery." ACS Nano, vol. 7, pp. 4194-4201 (2013).
Gu et al., "Glucose-Responsive Microgels Integrated with Enzyme Nanocapsules for Closed-Loop Insulin Delivery." ACS Nano, vol. 7, pp. 6758-6766 (2013).
Hu et al., "H2O2-Responsive Vesicles Integrated with Transcutaneous Patches for Glucose-Mediated Insulin Delivery." ACS Nano, vol. 11, pp. 613-620 (2017).
Ishihara et al., "Glucose Induced Permeation Control of Insulin through a Complex Membrane Consisting of Immobilized Glucose Oxidase and a Poly(amine)." Poly. J., vol. 16, pp. 625-631 (1984).
Ito et al., "An insulin-releasing system that is responsive to glucose." J. Control. Release, vol. 10, pp. 195-203 (1989).
Kataoka et al., "Totally Synthetic Polymer Gels Responding to External Glucose Concentration: Their Preparation and Application to On-Off Regulation of Insulin Release." J. Am. Chem. Soc., vol. 120, pp. 12694-12695 (1998).
Kim et al., "Glucose-Responsive Disassembly of Polymersomes of Sequence-Specific Boroxole-Containing Block Copolymers under Physiologically Relevant Conditions." ACS Macro Letters, vol. 1, pp. 1194-1198 (2012).
Kost et al., "Ultrasound-enhanced polymer degradation and release of incorporated substances." Proc. Natl. Acad. Sci. USA, vol. 86, pp. 7663-7666 (1989).
Liang et al., "A self-assembled molecular team of boronic acids at the gold surface for specific capture of cis-diol biomolecules at neutral pH." Chem. Commun., vol. 47, pp. 2255-2257 (2011).
Lu et al., "Bioresponsive materials." Nat. Rev. Mater., vol. 2(1), pp. 1-17 (2017).
Ma et al., "Phenylboronic Acid-Based Complex Micelles with Enhanced Glucose-Responsiveness at Physiological pH by Complexation with Glycopolymer." Biomacromolecules, vol. 13, pp. 3409-3417 (2012).
Matsumoto et al., "A Synthetic Approach Toward a Self-Regulated Insulin Delivery System." Angew. Chem. Int. Edit., vol. 51, pp. 2124-2128 (2012).
Matsumoto et al., "Glucose-Responsive Polymer Gel Bearing Phenylborate Derivative as a Glucose-Sensing Moiety Operating at the Physiological pH." Biomacromolecules, vol. 5, pp. 1038-1045 (2004).
Matsumoto et al., "Swelling and Shrinking Kinetics of Totally Synthetic, Glucose-Responsive Polymer Gel Bearing Phenylborate Derivative as a Glucose-Sensing Moiety." Macromolecules, vol. 37, pp. 1502-1510 (2004).
Mo et al., "Emerging micro- and nanotechnology based synthetic approaches for insulin delivery." Chemical Society Reviews, vol. 43, pp. 3595-3629 (2014).
DCCT/EDIC Study Research Group, N. Engl. J. Med., vol. 353, p. 2643-2653 (2005).
Obaidat et al., "Characterization of Glucose Dependent Gel-Sol Phase Transition of the Polymeric Glucose-Concanavalin A Hydrogel System." Pharm. Res., vol. 13, pp. 989-995 (1996).
Ohkubo et al., "Intensive insulin therapy prevents the progression of diabetic microvascular complications in Japanese patients with non-insulin-dependent diabetes mellitus: a randmized prospective 6-year study." Diabetes Research and Clinical Practice, vol. 28, pp. 103-117 (1995).
Owens et al., "Insulins today and beyond." Lancet, vol. 358, p. 739-746 (2001).
Park et al., "Multi-arm histidine copolymer for controlled release of insulin from poly(lactide-co-glycolide) microsphere," Biomaterials, vol. 33, pp. 8848-8857 (2012).
Payyappilly et al., "Thermoresponsive biodegradable PEG-PCL-PEG based injectable hydrogel for pulsatile insulin delivery." J. Biomed. Mater. Res. A, vol. 102, pp. 1500-1509 (2014).
Peppas et al., "Physiochemical Foundations and Structural Design of Hydrogels in Medicine and Biology." Annu. Rev. Biomed. Eng., vol. 2, pp. 9-29 (2000).
Pickup et al., "Nanomedicine and its potential in diabetes research and practice." Diabetes—Metabolism Research and Reviews, vol. 24, pp. 604-610 (2008).
Podual et al., "Dynamic behavior of glucose oxidase-containing microparticles of poly(ethylene glycol)-grafted cationic hydrogels in an environment of changing pH." Biomaterials, vol. 21, pp. 1439-1450 (2000).
Podual et al., "Glucose-sensitivity of glucose oxidase-containing cationic copolymer hydrogels having poly(ethylene glycol) grafts." J. Control. Release, vol. 67, pp. 9-17 (2000).
Podual et al., "Preparation and dynamic response of cationic coploymer hydrogels containing glucose oxidase." Polymer, vol. 41, pp. 3975-3983 (2000).
Rasool et al., "Synthesis and characterization of novel pH-, ionic strength and temperature-sensitive hydrogel for insulin delivery." Polymer, vol. 51, pp. 1687-1693 (2010).
Ren et al., "Ring-Opening Polymerization with Synergistic Co-monomers: Access to a Boronate-Functionalized Polymeric Monolith for the Specific Capture of cis-Diol-Containing Biomolecules under Neutral Conditions." Agnew. Chem. Int. Edit., vol. 48, pp. 6704-6707 (2009).
Reschel et al., "Physical properties and in vitro transfection efficiency of gene delivery vectors based on complexes of DNA with synthetic polycations." J. Control. Release, vol. 81, pp. 201-217 (2002).
Saslawski et al., "Magnetically responsive microspheres for the pulsed delivery of insulin." Life Sci., vol. 42, pp. 1521-1528 (1988).
Shiino et al., "Amine containing phenylboronic acid gel for glucose-responsive insulin release under physiological pH." J. Control. Release, vol. 37, pp. 269-276 (1995).
Springsteen et al., "A detailed examination of boronic acid-diol complexation." Tetrahedron, vol. 58, pp. 5291-5300 (2002).
Stumvoll et al., "Type 2 diabetes: principles of pathogenesis and therapy." Lancet, vol. 365, pp. 1333-1346 (2005).
Tabak et al., "Prediabetes: a high-risk state for diabetes development." Lancet, vol. 379, pp. 2279-2290 (2012).
Timko et al., "Near-infrared-actuated devices for remotely controlled drug delivery." Proc. Natl. Acad. Sci. USA, vol. 111, pp. 1349-1354 (2014).
Veiseh et al., "Managing diabetes with nanomedicine: challenges and opportunities." Nature Reviews Drug Discovery, vol. 14(1), pp. 45-57 (2015).
Yan et al., "The relationship among pKa, pH, and binding constants in the interactions between boronic acids and diols—it is not as simple as it appears." Tetrahedron, vol. 60, pp. 11205-11209 (2004).
Yang et al., "Glucose-responsive complex micelles for self-regulated release of insulin under physiological conditions." Soft Matter, vol. 9, pp. 8589-8599 (2013).
Yao et al., "Glucose-Responsive Vehicles Containing Phenylborate Ester for Controlled Insulin Release at Neutral pH." Biomacromolecules, vol. 13, pp. 1837-1844 (2012).
Yu et al., "Hypoxia and H2O2 Dual-Sensitive Vesicles for Enhanced Glucose-Responsive Insulin Delivery." Nano Lett., vol. 17, pp. 733-739 (2017).
Yu et al., "Microneedle-array patches loaded with hypoxia-sensitive vesicles provide fast glucose-responsive insulin delivery." Proc. Natl. Acad. Sci. USA, vol. 112, pp. 8260-8265 (2015).
Zhao et al., "Mesoporous Silica Nanoparticle-Based Double Drug Delivery System for Glucose-Responsive Controlled Release of Insulin and Cyclic AMP." J. Am. Chem. Soc., vol. 131, pp. 8398-8400 (2009).

(56) References Cited

OTHER PUBLICATIONS

Communication of European Publication Number Corresponding to Application No. 18882215.9-1112 dated Sep. 2, 2020.
International Preliminary Report on Patentability corresponding to International Patent Application No. PCT/US2018/061953 dated May 26, 2020.
Office Action corresponding to Japanese Patent Application No. 2020-545087 dated Jan. 10, 2023.
Office Action and Search Report corresponding to Chinese Patent Application No. 201800870877 dated Jan. 20, 2023.
Park et al., "Ultrasound Mediated Transdermal Insulin Delivery in Pigs Using a Lightweight Transducer," Pharm. Res., vol. 24, pp. 1396-1401 (2007).
Wang et al., "Red Blood Cells for Glucose-Responsive Insulin Delivery," Adv. Mater., vol. 29, Article ID 1606617 (2017).

* cited by examiner

POLY(EDAAx-FPBAy)
pH=7.4
[GLUCOSE] ↑

CHARGE-SWITCHABLE POLYMERIC DEPOT FOR GLUCOSE-TRIGGERED INSULIN DELIVERY WITH ULTRAFAST RESPONSE

RELATED APPLICATIONS

This application is a national stage filing of PCT International Application No. PCT/US2018/061953, filed Nov. 20, 2018, incorporated herein by reference in its entirety, which claims priority to and the benefit of U.S. Provisional Application Ser. No. 62/589,091 filed Nov. 21, 2017; the disclosure of which is incorporated herein by reference in its entirety.

TECHNICAL FIELD

The presently disclosed subject matter relates to compositions for glucose-responsive delivery of insulin and/or other negatively charged therapeutic agents. The composition can comprise a positively charged glucose-responsive polymer or a complex of the polymer and a negatively charged therapeutic agent, such as an insulin or a bioactive derivative thereof. The presently disclosed subject matter further relates to pharmaceutical compositions, microneedles, and microneedle arrays of the complexes; to methods of preparing the compositions; and to methods of delivering insulin to a subject in need thereof.

Abbreviations

° C.=degrees Celsius
%=percentage
μL=microliter
μm=micrometer or micron
a.u.=arbitrary units
BGL=blood glucose level
Boc=tert-butoxycarbonyl
CD=circular dichroism
DI=deionized
dL=deciliter
DLS=dynamic light scattering
EDA=ethylene diamine
EDAA=ethylene diamine acrylamide
ELISA=enzyme linked immunosorbent assay
FPBA=fluorophenylboronicacid
h=hour
IPGTT=intraperitoneal glucose tolerance test
IU=international units
kDa=kilodalton
kg=kilogram
MBA=N,N'-methylene bisacrylamide
mg=milligram
m-HA=acrylate-modified hyaluoric acid
min=minutes
mL=milliliter
mM=millimolar
mmol=millimoles
$M_n$=number-average molecular weight
MN=microneedle
N=Normal
nm=nanometer
NMR=nuclear magnetic resonance
PBA=phenylboronic acid
PBS=phosphate buffered saline
PEG=poly(ethylene glycol)
RhB=rhodamine B
S.D.=standard deviation
STZ=streptozotocin
TEM=transmission electron microscope
UV=ultraviolet
wt=weight

BACKGROUND

Diabetes mellitus is a group of metabolic diseases characterized by accumulation of glucose in the blood. See Pickup et al., Diabetes-Metabolism Research and Reviews, 24, 604-610 (2008); and Stumvoll et al., Lancet, 365, 1333-1346 (2005). As of 2014, 387 million people suffer from diabetes worldwide, and the number is estimated to be 592 million by 2035. See Mo et al., Chemical Society Reviews, 43, 3595-3629 (2014); and Tabák et al., Lancet, 379, 2279-2290 (2012). Insulin replacement is generally considered essential for type 1 and advanced type 2 diabetic patients. See Owens et al., Lancet, 358, 739 (2001); and Mo et al., Chemical Society Reviews, 43, 3595 (2014). Intensive insulin therapy of type 1 diabetes is associated with improved glycemia control and decreased risk of long-term complications. See Control et al., N. Engl. J. Med., 329, 977 (1993); and Nathan, N. Engl. J. Med., 353, 2643 (2005). But, frequent insulin dosing and boluses, either through injection or through subcutaneous insulin infusion, can also lead to an increasing risk of hypoglycemia, or dangerously low levels of glucose in the blood. Episodes of hypoglycemia are characterized by behavioral and cognitive disturbance, and if untreated, can progress to seizure, coma, and even death. See Ohkubo et al., Diabetes Research and Clinical Practice, 28, 103 (1995). Despite treatment advances in electronic/mechanical insulin delivery devices and in chemical approaches to insulin delivery, hypoglycemia still remains a concern, even in a closed-loop insulin delivery system. See Veiseh et al., Nature Reviews Drug Discovery, 14, 45 (2015).

Accordingly, there is still a need for additional insulin delivery systems and related compositions, particularly for "closed-loop" delivery systems that can deliver insulin to a subject rapidly in response to changes in blood glucose levels and with little to no pain.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

In some embodiments, the presently disclosed subject matter provides a composition comprising: (a) a positively-charged polymer comprising (i) ammonium groups and (ii) glucose-binding groups; and (b) insulin or a bioactive derivative thereof, optionally recombinant human insulin. In some embodiments, the glucose-binding group comprises an arylboronic acid group. In some embodiments, the arylboronic acid group is a phenylboronic acid group, optionally wherein the phenylboronic acid group is a halophenylboronic acid group, further optionally wherein the halophenylboronic acid group is a fluorophenylboronic acid group.

In some embodiments, the positively charged polymer has a polyacrylamide backbone comprising a plurality of side chains comprising an ammonium group and a plurality of side chains comprising a glucose-binding group. In some embodiments, the polymer has a structure of formula (I):

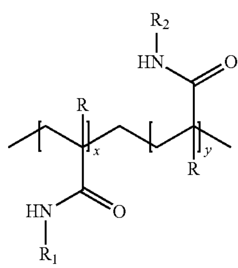

wherein: x and y are each integers greater than 1, wherein the sum of integers x and y is at least about 10; and wherein the ratio of x to y is between about 7:3 and about 1:5; R is H or alkyl, optionally $C_1$-$C_6$ alkyl; $R_1$ is a protonated aminoalkyl group; and $R_2$ is a group comprising an arylboronic acid.

In some embodiments, $R_1$ has the structure $-L-NH_3^+$, wherein L is a $C_1$-$C_6$ straight or branched, substituted or unsubstituted alkylene group, optionally wherein L is —$CH_2CH_2$—. In some embodiments, $R_2$ has the structure $-L_1$-NH—C(═O)—$R_3$, wherein $L_1$ is a $C_1$-$C_6$ straight or branched, substituted or unsubstituted alkylene group, optionally wherein $L_1$ is —$CH_2CH_2$—; and wherein $R_3$ is an arylboronic acid group, optionally wherein $R_3$ is a phenylboronic acid group, further optionally wherein $R_3$ is a fluorophenylboronic acid group or other halophenylboronic acid group. In some embodiments, the ratio of x to y is about 2:3.

In some embodiments, the composition comprises a weight ratio of positively-charged polymer (a) to insulin or bioactive derivative thereof (b) of between about 2:1 and about 1:4. In some embodiments, the weight ratio of (a) to (b) is about 1:1.

In some embodiments, the presently disclosed subject matter provides a nanoparticle or microparticle comprising a composition comprising: (a) a positively-charged polymer comprising (i) ammonium groups and (ii) glucose-binding groups; and (b) insulin or a bioactive derivative thereof. In some embodiments, the nanoparticle or microparticle has a diameter of between about 0.1 micrometers (μm) and about 1000 μm, optionally about 50 μm.

In some embodiments, the presently disclosed subject matter provides a microneedle array comprising a nanoparticle or microparticle comprising a composition comprising: (a) a positively-charged polymer comprising (i) ammonium groups and (ii) glucose-binding groups; and (b) insulin or a bioactive derivative thereof, optionally wherein said microneedle array comprises a plurality of microneedles, wherein each of said plurality of microneedles has a length of between about 20 and about 1000 micrometers, further optionally wherein each of the plurality of microneedles has a length of about 600 micrometers. In some embodiments, the presently disclosed subject matter provides a skin patch comprising the microneedle array, optionally wherein said patch comprises one or more backing layers and/or skin compatible adhesives.

In some embodiments, the presently disclosed subject matter provides a pharmaceutical formulation comprising a pharmaceutically acceptable carrier and a composition comprising: (a) a positively-charged polymer comprising (i) ammonium groups and (ii) glucose-binding groups; and (b) insulin or a bioactive derivative thereof, and/or a nanoparticle or microparticle comprising said composition.

In some embodiments, the presently disclosed subject matter provides a method of delivering insulin or a bioactive derivative thereof to a subject in need thereof, the method comprising administering a skin patch or a pharmaceutical formulation comprising a composition comprising: (a) a positively-charged polymer comprising (i) ammonium groups and (ii) glucose-binding groups; and (b) insulin or a bioactive derivative thereof; or nanoparticles or microparticles comprising said composition, to the subject. In some embodiments, the subject is a mammal, optionally a human. In some embodiments, the subject has type 1 or type 2 diabetes.

In some embodiments, the administering comprises administering the pharmaceutical formulation via subcutaneous injection. In some embodiments, the skin patch or pharmaceutical formulation releases insulin at a rate that corresponds directly to blood glucose levels of the subject.

In some embodiments, the presently disclosed subject matter provides a method of treating diabetes in a subject in need thereof, wherein the method comprises administering a skin patch or a pharmaceutical formulation comprising a composition comprising: (a) a positively-charged polymer comprising (i) ammonium groups and (ii) glucose-binding groups; and (b) insulin or a bioactive derivative thereof; or nanoparticles or microparticles comprising said composition, to the subject. In some embodiments, the administration is performed once a day.

In some embodiments, the presently disclosed subject matter provides a composition comprising a polyacrylamide polymer comprising pendent aminoalkyl groups, optionally protonated aminoalkyl groups, and pendent halophenylboronic acid groups, optionally pendent fluorophenylboronic acid groups. In some embodiments, the composition comprises a polymer having a structure of formula (II):

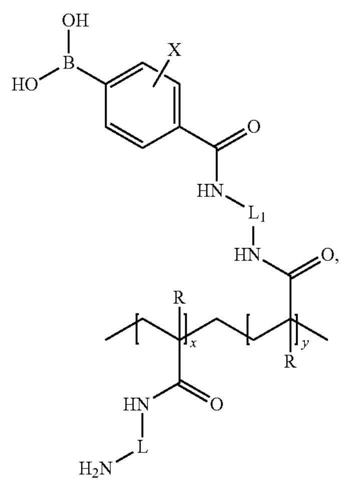

wherein: x and y are each integers greater than 5 and having a ratio between about 7:3 x:y and about 1:5 x:y; R is H or alkyl, optionally $C_1$-$C_6$ alkyl; L and $L_1$ are each alkylene;

and X is halo, optionally fluoro; optionally wherein the —$NH_2$ groups are protonated.

In some embodiments, the polymer has a structure of formula (III):

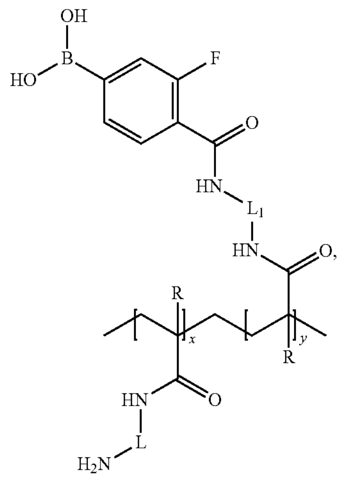

wherein: x and y are each integers greater than 5 and having a ratio between about 7:3 x:y and about 1:5 x:y; R is H or alkyl, optionally $C_1$-$C_6$ alkyl; and L and $L_1$ are each alkylene independently selected from $C_1$-$C_5$ alkylene; optionally wherein the —$NH_2$ groups are protonated.

In some embodiments, L and/or $L_1$ are —$CH_2CH_2$—. In some embodiments, R is H. In some embodiments, the ratio between x and y is about 2:3. In some embodiments, the polymer has a molecular weight of between about 1 KDa and about 30 KDa.

Accordingly, it is an object of the presently disclosed subject matter to provide glucose-responsive compositions for the delivery of insulin, as well as methods of preparing and using said compositions.

An object of the presently disclosed subject matter having been stated hereinabove, and which is achieved in whole or in part by the presently disclosed subject matter, other objects will become evident as the description proceeds when taken in connection with the accompanying drawings and examples as best described herein below.

Figure 3A:
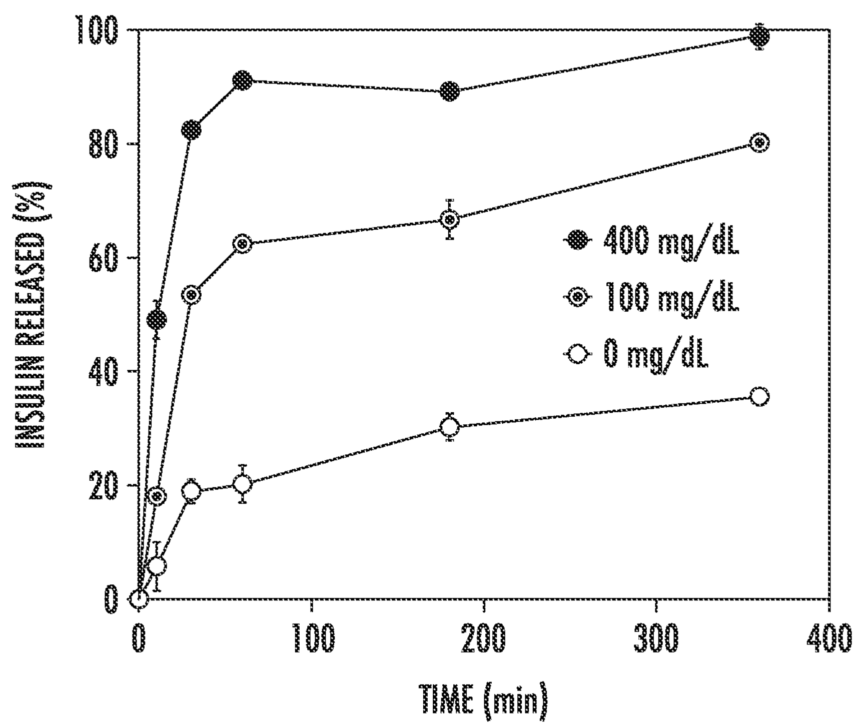

FIG. 3A is a graph showing glucose-dependent insulin release (percentage (%) versus time (in minutes (min)) from a complex of 1:2 (weight:weight) insulin to poly(ethylene diamine acrylamide) (poly(EDAA)) where 60 percent of the pendent amino groups are grafted to fluorophenyl boronic acid (FPBA) groups (i.e., poly($EDAA_{0.4}$-$FPBA_{0.6}$). Insulin release is measured at three different glucose concentrations (0 milligrams/deciliter (mg/dL) (unfilled circles), 100 mg/dL (half-filled circles) and 400 mg/dL (filled circles)). Error bars represent the standard deviation (S.D.) of three independent experiments (n=3).

Figure 3B:
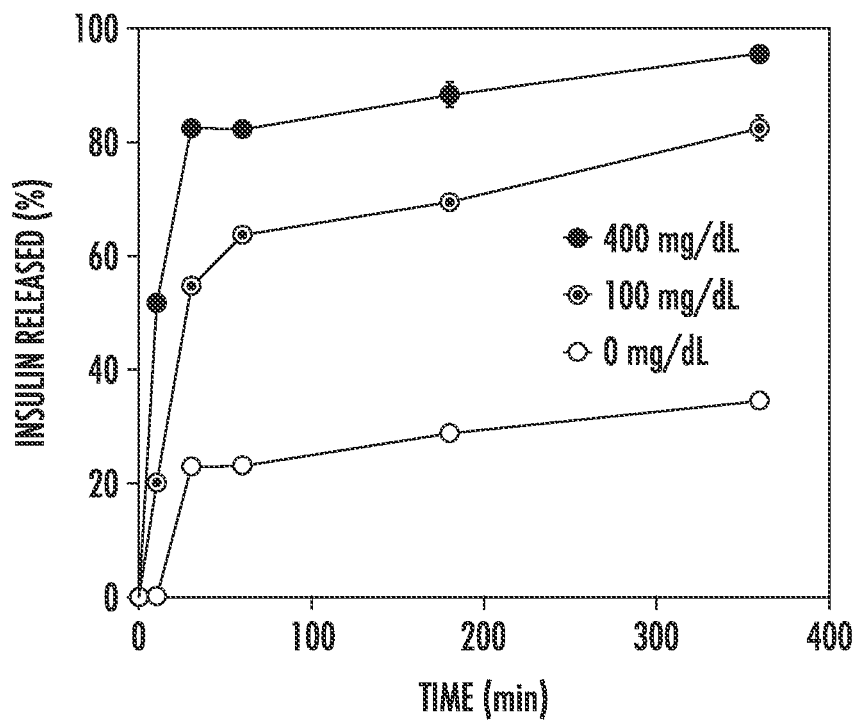

FIG. 3B is a graph showing glucose-dependent insulin release (percentage (%) versus time (in minutes (min)) from a complex of 1:4 (weight:weight) insulin to poly(ethylene diamine acrylamide) (poly(EDAA)) where 60 percent of the pendent amino groups are grafted to fluorophenyl boronic acid (FPBA) groups (i.e., poly($EDAA_{0.4}$-$FPBA_{0.6}$). Insulin release is measured at three different glucose concentrations (0 milligrams/deciliter (mg/dL) (unfilled circles), 100 mg/dL (half-filled circles) and 400 mg/dL (filled circles)). Error bars represent the standard deviation (S.D.) of three independent experiments (n=3).

Figure 3C:
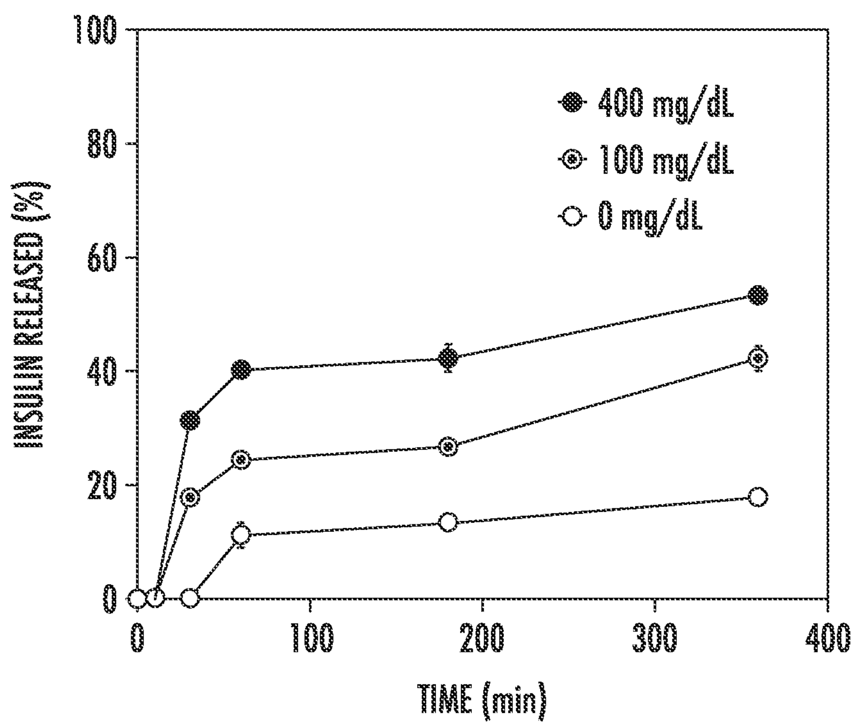

FIG. 3C is a graph showing glucose-dependent insulin release (percentage (%) versus time (in minutes (min)) from a complex of 2:1 (weight:weight) insulin to poly(ethylene diamine acrylamide) (poly(EDAA)) where 60 percent of the pendent amino groups are grafted to fluorophenyl boronic acid (FPBA) groups (i.e., poly($EDAA_{0.4}$-$FPBA_{0.6}$). Insulin release is measured at three different glucose concentrations (0 milligrams/deciliter (mg/dL) (unfilled circles), 100 mg/dL (half-filled circles), and 400 mg/dL (filled circles)). Error bars represent the standard deviation (S.D.) of three independent experiments (n=3).

Figure 3D:
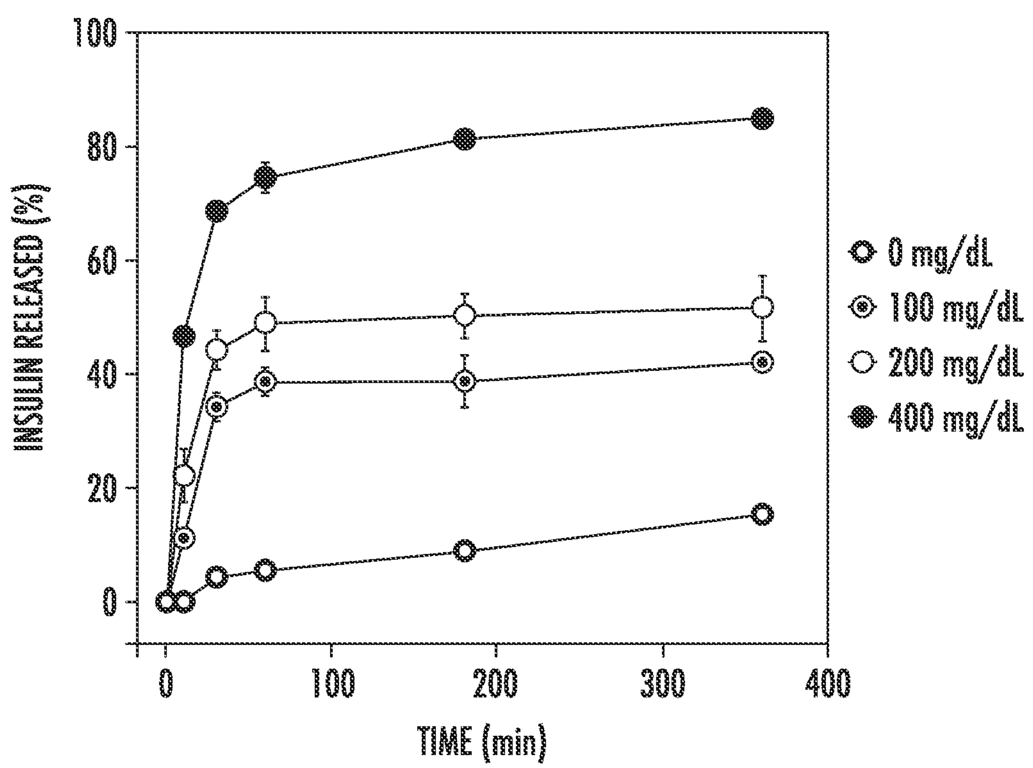

FIG. 3D is a graph showing glucose-dependent insulin release (percentage (%) versus time (in minutes (min)) from a complex of equal weight insulin to poly(ethylene diamine acrylamide) (poly(EDAA)) where 60 percent of the pendent amino groups are grafted to fluorophenyl boronic acid (FPBA) groups (i.e., poly($EDAA_{0.4}$-$FPBA_{0.6}$). Insulin release is measured at four different glucose concentrations (0 milligrams/deciliter (mg/dL) (circles with heavy perimeter and unfilled center), 100 mg/dL (circles with filled center), 200 mg/dL (unfilled circles), and 400 mg/dL (filled circles)). Error bars represent the standard deviation (S.D.) of three independent experiments (n=3).

Figure 3E:
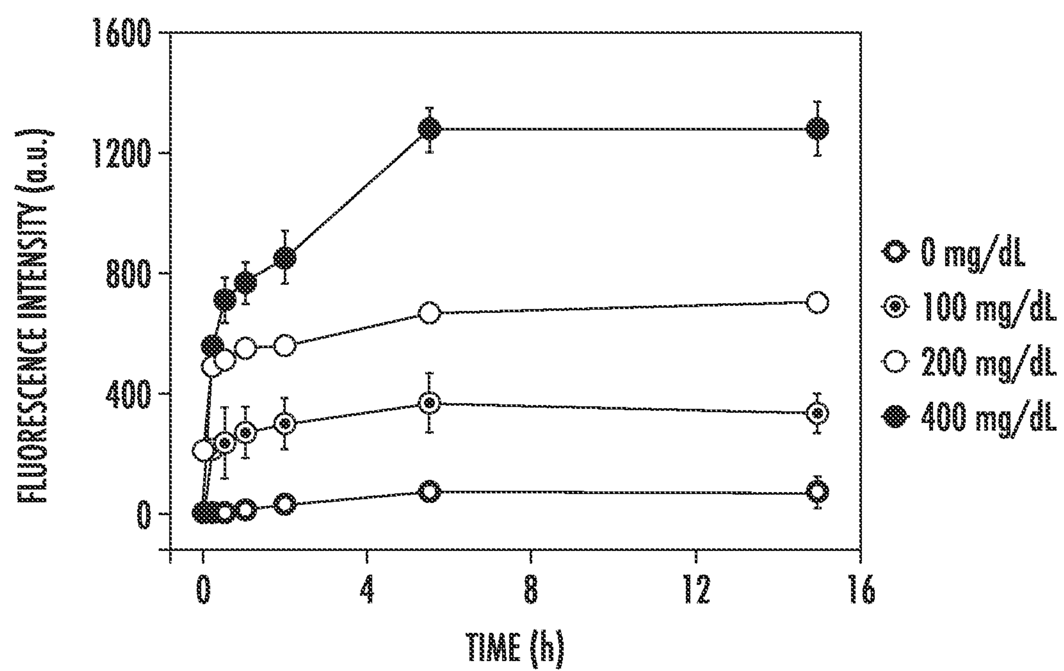

FIG. 3E is a graph showing glucose-dependent fluorescence intensity (measured in arbitrary units (a.u.)) as a function of time (in hours (h)) in supernatants of a complex of equal weight insulin to poly(ethylene diamine acrylamide) (poly(EDAA)) where 60 percent of the pendent amino groups are grafted to fluorophenyl boronic acid (FPBA) groups (i.e., poly($EDAA_{0.4}$-$FPBA_{0.6}$). Complexes were placed in one of four solutions having different glucose concentrations (0 milligrams/deciliter (mg/dL) (circles with heavy perimeter and unfilled center), 100 mg/dL (circles with filled center), 200 mg/dL (unfilled circles), and 400 mg/dL (filled circles)). Error bars represent the standard deviation (S.D.) of three independent experiments (n=3).

Figure 3F:
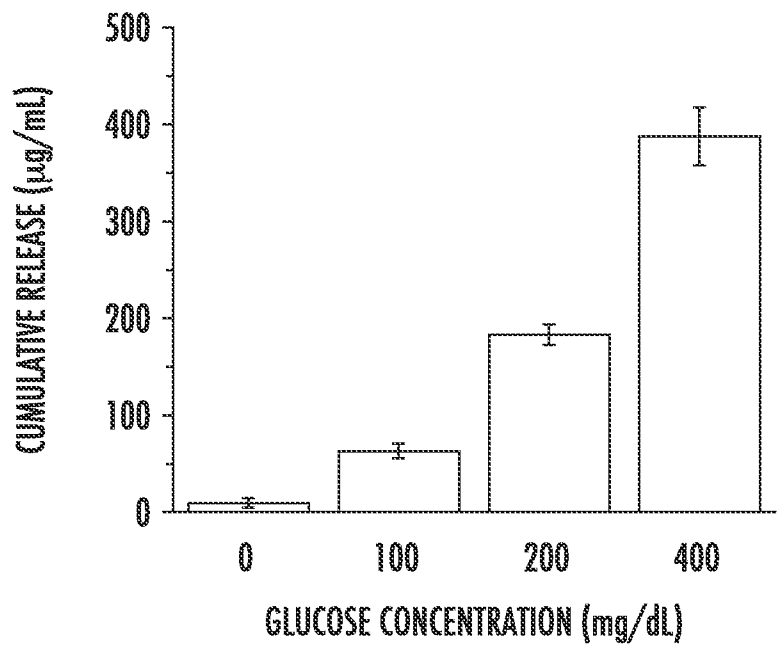

FIG. 3F is a graph showing the cumulative insulin release profile of a complex of equal weight insulin to poly(ethylene diamine acrylamide) (poly(EDAA)) where 60 percent of the pendent amino groups are grafted to fluorophenyl boronic acid (FPBA) groups (i.e., poly($EDAA_{0.4}$-$FPBA_{0.6}$). The complex was incubated in one of four solutions having different glucose concentrations (0 milligrams/deciliter (mg/dL), 100 mg/dL, 200 mg/dL, and 400 mg/dL) for 10 minutes. Cumulative insulin release is measured in micrograms per milliliters (μg/mL). Error bars represent the standard deviation (S.D.) of three independent experiments (n=3).

Figure 3G:
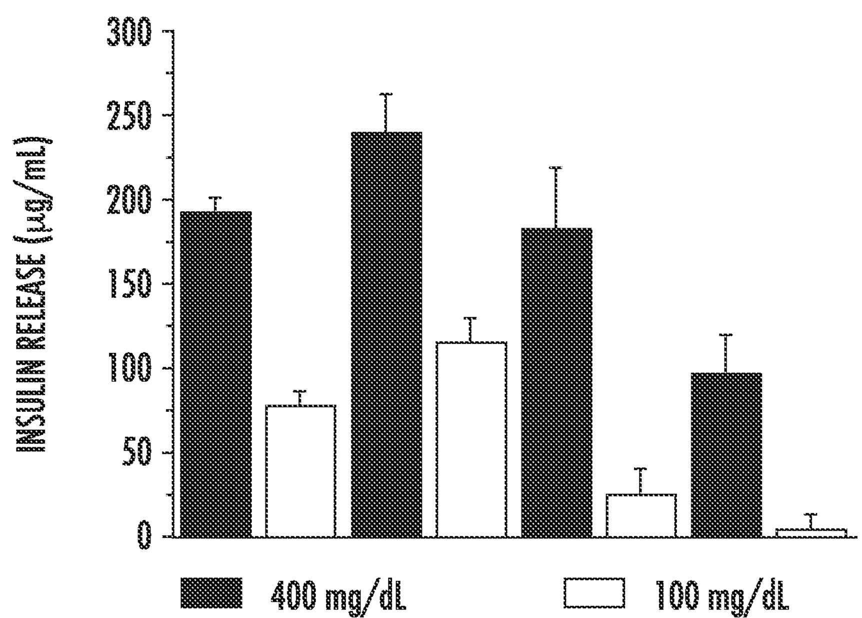

FIG. 3G is a graph showing the pulsatile insulin release profile of a complex of equal weight insulin to poly(ethylene diamine acrylamide) (poly(EDAA)) where 60 percent of the pendent amino groups are grafted to fluorophenyl boronic acid (FPBA) groups (i.e., poly($EDAA_{0.4}$-$FPBA_{0.6}$) as a function of glucose concentration. The complex was incubated in alternating solutions comprising 400 milligrams per deciliter (mg/dL) glucose (filled bars) or 100 mg/dL glucose (unfilled bars). The glucose concentration was changed every two minutes. Insulin release is measured in micrograms per milliliters (μg/mL). Error bars represent the standard deviation (S.D.) of three independent experiments (n=3).

Figure 4A:
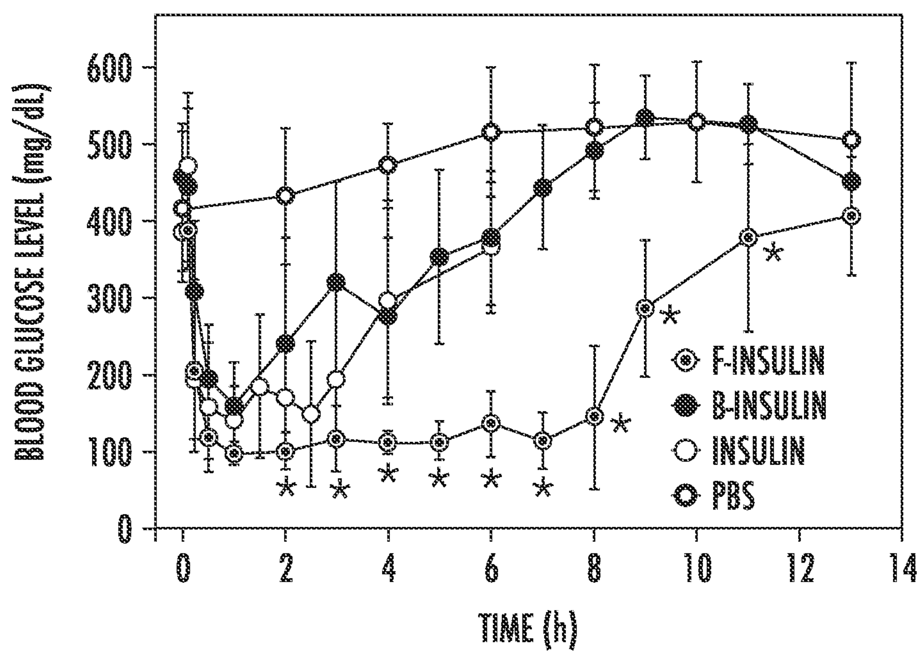

FIG. 4A is a graph showing blood glucose levels (in microgram per deciliter (mg/dL)) in a type 1 diabetic mouse model where mice were treated with free insulin (Insulin; unfilled circles); F-insulin (i.e., a polymer-insulin complex comprising an equal weight insulin and polymer, where the polymer is poly(ethylene diamine acrylamide) (poly (EDAA)) where 60 percent of the pendent amino groups are grafted to fluorophenyl boronic acid (FPBA) groups (i.e., poly($EDAA_{0.4}$-$FPBA_{0.6}$)); circles with filled center); or B-insulin (i.e., a polymer-insulin complex comprising an equal weight of insulin and polymer, where the polymer is poly(ethylene diamine acrylamide) (poly(EDAA)) where 60 percent of the pendent amino groups are grafted to phenyl boronic acid (PBA) groups (i.e., poly($EDAA_{0.4}$-$PBA_{0.6}$)); filled circles). Phosphate buffered saline (PBS) was used as a control (circles with heavy perimeter and unfilled center). The insulin dose was set to 80 international units per kilogram (IU/kg). Error bars represent the standard deviation (S.D.) of five independent experiments (n=5). $^*P<0.05$ for administration with F-insulin compared with B-insulin.

Figure 4B:
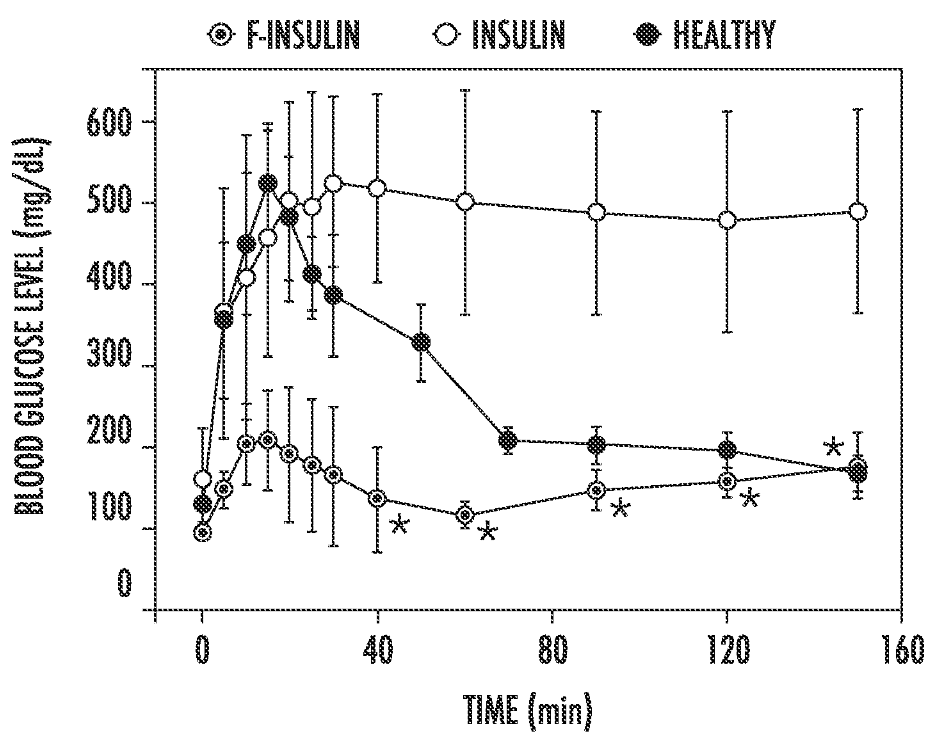

FIG. 4B is a graph showing results of in vivo intraperitoneal glucose tolerance tests (IPGTT) in a diabetic mouse model for up to three hours after treatment with F-insulin (i.e., a polymer-insulin complex comprising an equal weight insulin and polymer, where the polymer is poly(ethylene diamine acrylamide) (poly(EDAA)) where 60 percent of the pendent amino groups are grafted to fluorophenyl boronic acid (FPBA) groups (i.e., poly($EDAA_{0.4}$-$FPBA_{0.6}$)); half-filled circles) or free insulin (unfilled circles). Healthy mice were used as a control (filled circles). Blood glucose levels are measured in milligrams per deciliter (mg/dL) and shown from time 0 (time of administration of the F-insulin or free insulin) to up to 160 minutes (min) after administration. Error bars represent the standard deviation (S.D.) of five independent experiments (n=5). $^*P<0.05$ for treatment with F-insulin compared with free insulin.

Figure 4C:
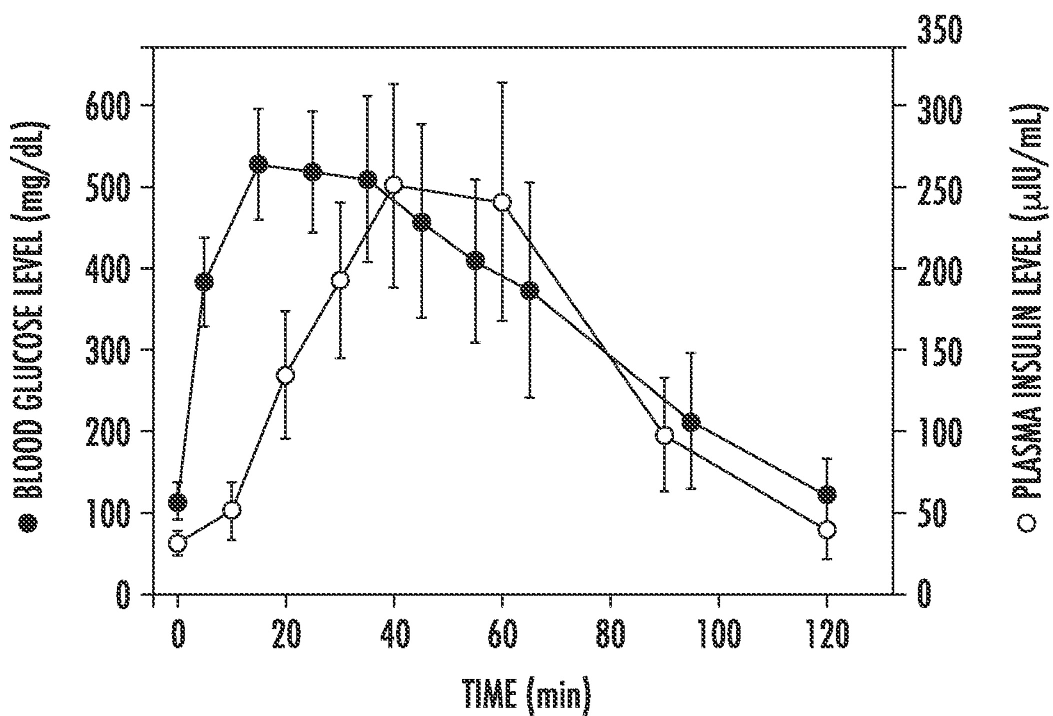

FIG. 4C is a graph showing in vivo glucose-responsive release of insulin triggered by intraperitoneal glucose injection at four hours post-treatment with F-insulin at a dose of 80 international units per kilogram (IU/kg). Data is provided for both blood glucose level (in milligrams per deciliter (mg/dL) (filled circles) and plasma insulin level (in micro international units per milliliter (μIU/mL) (unfilled circles). Error bars represent the standard deviation (S.D.) of five independent experiments (n=5).

Figure 4D:
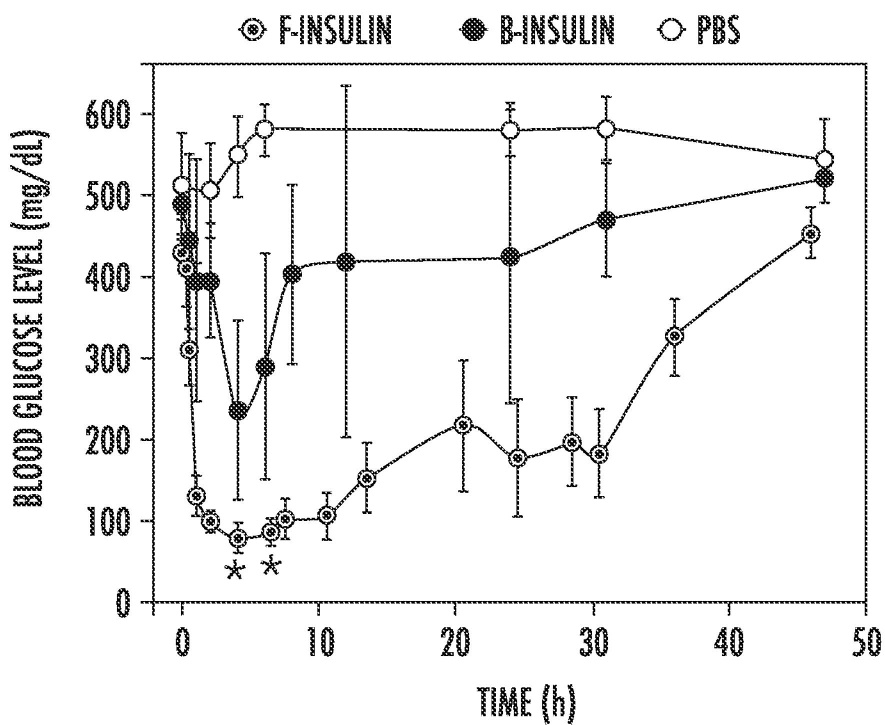

FIG. 4D is a graph showing blood glucose levels (in milligrams per deciliter) versus time (hours (h)) in a mouse model of type I diabetes after mice were subcutaneously injected with a gel loaded with F-insulin (half-filled circles) or B-insulin (filled circles). The insulin dose was set to 300 international units per kilogram (IU/kg). Treatment with phosphate buffered saline (PBS) (unfilled circles) was used as a control. Error bars represent the standard deviation (S.D.) of five independent experiments (n=5). *P<0.05 for treatment with F-insulin compared to B-insulin.

Figure 5A:
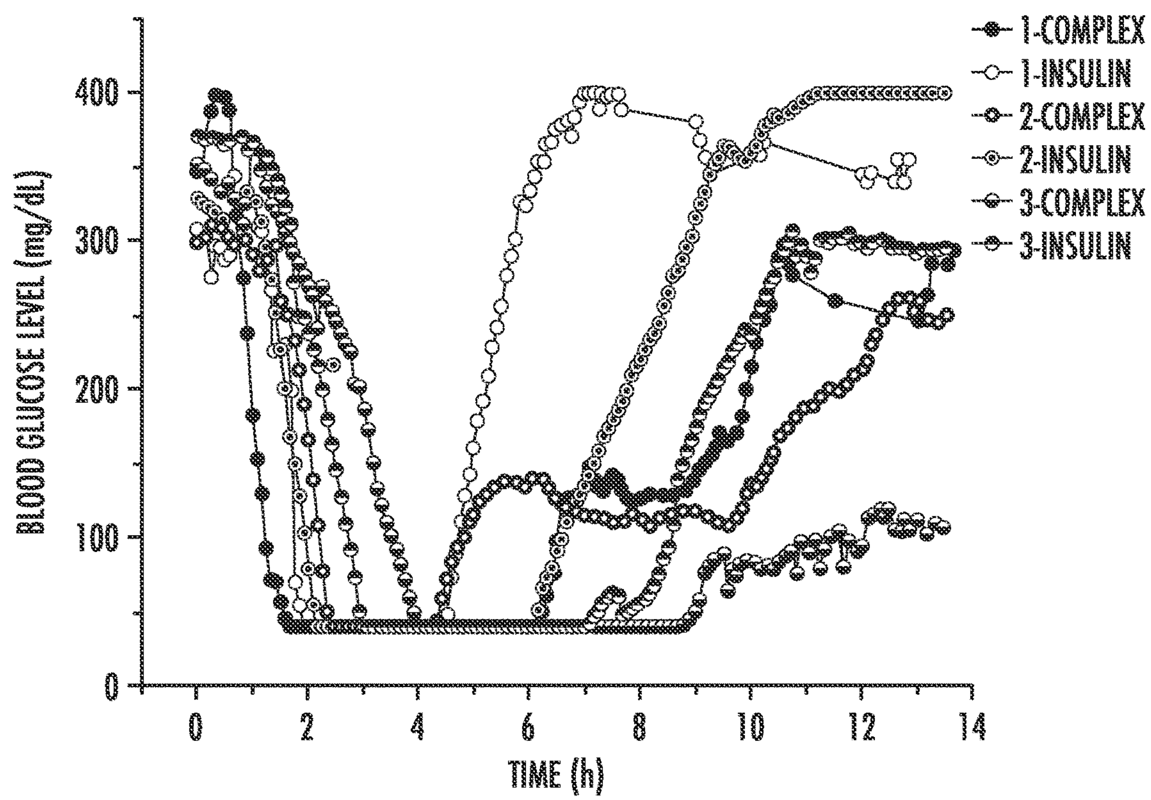

FIG. 5A is a graph showing blood glucose levels (BLGs, measured in milligrams per deciliter (mg/dL)) of type 1 diabetic minipigs treated with free insulin (1-Insulin (unfilled circles), 2-Insulin (circles with filled centers), or 3-Insulin (circles with top half filled)) or F-insulin (1-Complex (filled circles), 2-Complex (circles with heavy perimeter and unfilled center), or 3-Complex (circles with bottom half filled)). The insulin dose was set to 1 international unit per kilogram (IU/kg). Each curve represents the BLGs of a single pig followed for up to 14 hours (h) after administration of the free insulin or F-insulin.

Figure 5B:
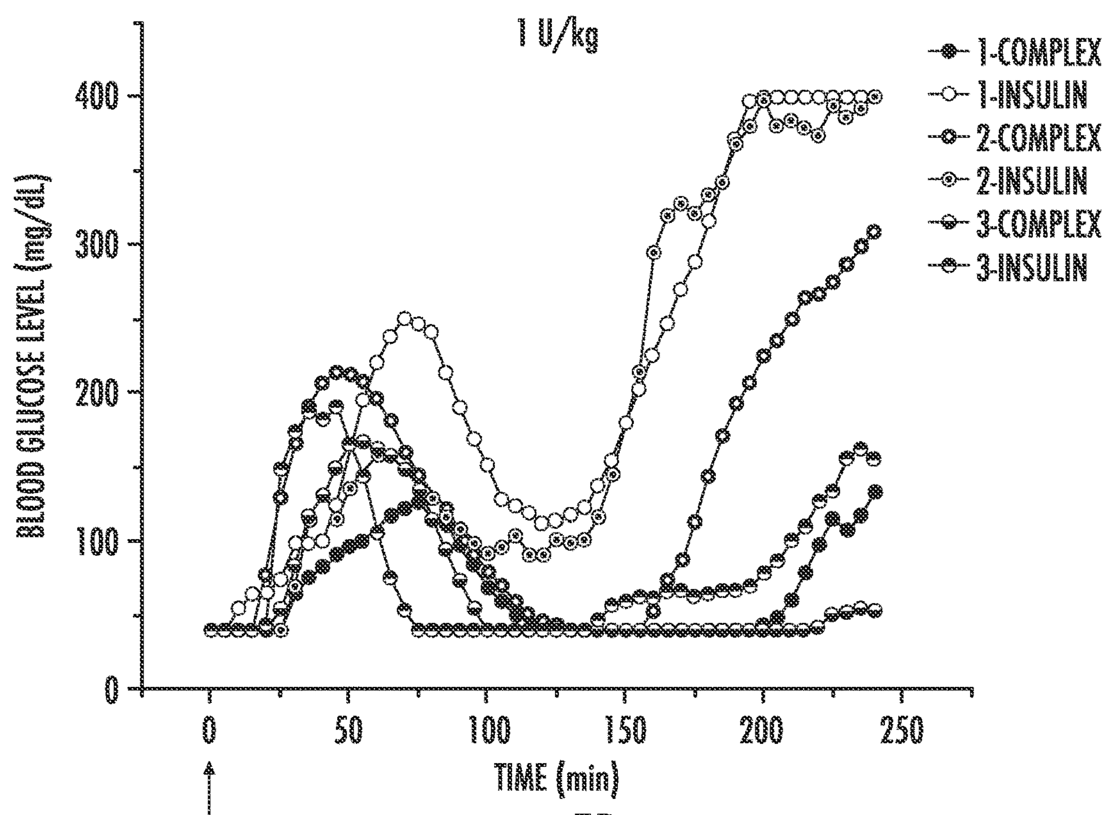

FIG. 5B is a graph showing results of an oral glucose tolerance test in type 1 diabetic minipigs at four hours post-treatment with 1 international unit per kilogram (IU/kg) free insulin (1-Insulin (unfilled circles), 2-Insulin (circles with filled centers), or 3-Insulin (circles with top half filled)) or F-insulin (1-Complex (filled circles), 2-Complex (circles with heavy perimeter and unfilled center), or 3-Complex (circles with bottom half filled). The arrow indicates the administration of glucose (0.5 grams per kilogram (g/kg)). Blood glucose levels (BLGs, measured in milligrams per deciliter (mg/dL) were followed in the pigs for up to 250 minutes (min) post glucose administration. Each curve represents the BLGs of a single pig.

Figure 6:
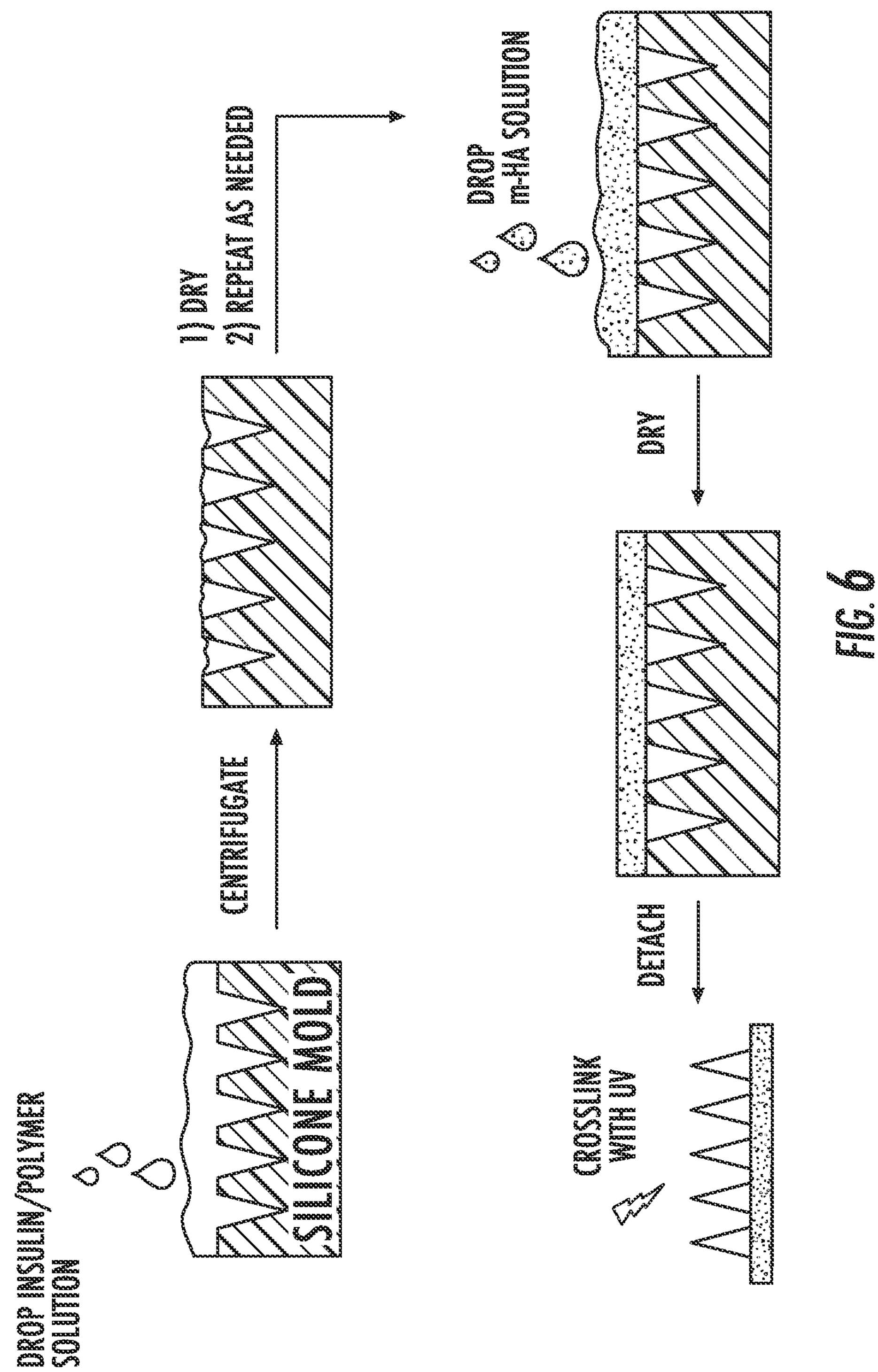

FIG. 6 is a schematic drawing of an exemplary process for preparing a glucose-responsive insulin delivery microneedle (MN) array patch comprising the presently disclosed insulin-polymer complexes using a silicone mold.

DETAILED DESCRIPTION

The presently disclosed subject matter will now be described more fully hereinafter with reference to the accompanying Examples and Drawings, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which the presently described subject matter belongs. All publications, patent applications, patents, and other references mentioned herein are incorporated by reference in their entirety.

Throughout the specification and claims, a given chemical formula or name shall encompass all active optical and stereoisomers, as well as racemic mixtures where such isomers and mixtures exist.

I. Definitions

While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. Thus, for example, reference to "a composition" or "a polymer" includes a plurality of such compositions or polymers, and so forth.

Unless otherwise indicated, all numbers expressing quantities of size, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about", when referring to a value or to an amount of size (i.e., diameter), weight, time, dose, concentration or percentage is meant to encompass variations of in one example ±20% or ±10%, in another example ±5%, in another example 1%, and in still another example ±0.1% from the specified amount, as such variations are appropriate to perform the disclosed methods.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. In some embodiments, "lower alkyl" can refer to $C_{1-6}$ or $C_{1-5}$ alkyl groups. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, nitro, amino, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

The term "aralkyl" refers to an -alkyl-aryl group, optionally wherein the alkyl and/or aryl group comprises one or more alkyl and/or aryl group substituents.

In some embodiments, the term "bivalent" refers to a group that can bond (e.g., covalently bond) or is bonded to two other groups, such as other alkyl, aralkyl, cycloalkyl, or aryl groups. Typically, two different sites on the bivalent group (e.g., two different atoms) can bond to groups on other molecules. For example, the bivalent group can be an alkylene group.

"Alkylene" can refer to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH═CH—CH═CH—; —CH═CH—$CH_2$—; —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons.

"Arylene" refers to a bivalent aryl group, which can be substituted or unsubstituted.

The term "aralkylene" refers to a bivalent group that comprises a combination of alkylene and arylene groups (e.g., -arylene-alkylene-, alkylene-arylene-alkylene-, arylene-alkylene-arylene-, etc.).

The term "acyl" refers to the —C(═O)R group, wherein R is H, alkyl, aralkyl or aryl, wherein the alkyl, aralkyl, or aryl group is optionally substituted with an alkyl and/or aryl group substituent.

The terms "carboxylate" and "carboxylic acid" can refer to the groups —C(═O)$O^-$ and —C(═O)OH, respectively. In some embodiments, "carboxylate" can refer to either the —C(═O)$O^-$ or —C(═O)OH group.

The term "amide" refers to the —C(═O)—NR— group, wherein R is H, alkyl, aralkyl or aryl.

The terms "amino" and "amine" as used herein refer to the group —$N(R)_2$ wherein each R is independently H, alkyl, substituted alkyl, aryl, substituted aryl, aralkyl, or substituted aralkyl. The terms "aminoalkyl" and "alkylamino" can refer to the group —R'—$N(R)_2$ wherein each R is H, alkyl, substituted alkyl, aralkyl, substituted aralkyl, aryl, or substituted aryl, and wherein R' is alkylene. "Arylamine" and "aminoaryl" refer to the group —R'—$N(R)_2$ wherein each R is H, alkyl, substituted alkyl, aralkyl, substituted aralkyl, aryl, or substituted aryl, and R' is arylene. The term "primary amine" refers to a group comprising a —$NH_2$ group.

The term "ammonium" as used herein refers to the group formed from a positively charged, tetra-substituted nitrogen, i.e., —$R'^{+}N(R)_3$ wherein each R is independently H, alkyl, substituted alkyl, aryl, substituted aryl, aralkyl, or substituted aralkyl and R' is alkylene, aralkylene or arylene. In some embodiments, the term "ammonium" refers to the positively charged group formed by the protonation of an amine group. In some embodiments, the term "ammonium" refers to a positively-charged, protonated primary amine group, i.e., a —*$NH_3$ group.

The terms "halo", "halide", or "halogen" as used herein refer to fluoro, chloro, bromo, and iodo groups.

The term "hydroxyl" refers to the —OH group.

The term "alkoxy" refers to a —OR group, wherein R is alkyl or substituted alkyl.

The term "boronic acid" as used herein refers to a group having the formula —B—$(OH)_2$.

The term "boronic acid ester" refers to the group —B—$(OR)_2$, wherein each R is independently alkyl, substituted alkyl, aralkyl, substituted aralkyl, aryl, or substituted aryl. In some embodiments, the two R groups together form an alkylene, aralkylene, or arylene group (e.g., ethylene).

The term "nanoparticle" as used herein refers to a structure having at least one region with a dimension (e.g., length, width, diameter, etc.) of less than about 1,000 nm and that comprises a positively-charged polymer (e.g., comprising ammonium groups and comprising glucose binding groups) and insulin or a bioactive derivative thereof. In some embodiments, the dimension is smaller (e.g., less than about 500 nm, less than about 250 nm, less than about 200 nm, less than about 150 nm, less than about 125 nm, less than about 100 nm, less than about 80 nm, less than about 70 nm, less than about 60 nm, less than about 50 nm, less than about 40 nm, less than about 30 nm or even less than about 20 nm).

The term "microparticle" as used herein refers to a structure having at least one region with a dimension (e.g., length, width, diameter, etc.) of less than about 1,000 μm and more than about 0.1 μm that comprises a positively-charged polymer (e.g., comprising ammonium groups and comprising glucose binding groups) and insulin or a bioactive derivative thereof. In some embodiments, the dimension is smaller (e.g., about 500 μm, about 250 μm, about 200 μm, about 150 μm, about 125 μm, about 100 μm, about 80 μm, about 70 μm, about 60 μm, about 50 μm, about 40 μm, about 30 μm, about 20 μm, or about 10 μm).

The micro- or nanoparticles can have any three-dimensional shape. In some embodiments, the particles are approximately spherical. In some embodiments, the particles are disc, cube or rod shaped. In some embodiments, the particles are irregularly shaped.

The term "diameter" is art-recognized and is used herein to refer to either the physical diameter or the hydrodynamic diameter. The diameter of an essentially spherical particle can refer to the physical or hydrodynamic diameter. As used herein, the diameter of a non-spherical particle can refer to the largest linear distance between two points on the surface of the particle. When referring to multiple particles, the diameter of the particles typically refers to the average diameter of the particles. Particle diameter can be measured using a variety of techniques in the art including, but not limited to, dynamic light scattering (DLS).

The term "microneedle" as used herein refers to a needle-like structure having at least one region with a dimension of less than about 1,000 microns (μm). In some embodiments, the term "microneedle" refers to a structure having a dimension between about 1 micron and about 1,000 microns (e.g., about 1, 5, 10, 25, 50, 75, 100, 200, 300, 400, 500, 600, 700, 800, 900 or about 1,000 microns).

As used herein, a "macromolecule" refers to a molecule of high relative molecular mass, the structure of which comprises the multiple repetition of units derived from molecules of low relative molecular mass, e.g., monomers and/or oligomers.

An "oligomer" refers to a molecule of intermediate relative molecular mass, the structure of which comprises a small plurality (e.g., 2, 3, 4, 5, 6, 7, 8, 9, or 10) of repetitive units derived from molecules of lower relative molecular mass.

As used herein, a "monomer" refers to a molecule that can undergo polymerization, thereby contributing constitutional units, i.e., an atom or group of atoms, to the essential structure of a macromolecule.

The terms "polymer" and "polymeric" refer to chemical structures that have repeating constitutional units (i.e., multiple copies of a given chemical substructure or "monomer unit"). As used herein, polymers can refer to groups having more than 10 repeating units and/or to groups wherein the repeating unit is other than methylene. Polymers can be formed from polymerizable monomers. A polymerizable monomer is a molecule that comprises one or more reactive moieties {e.g., siloxy ethers, hydroxyls, amines, vinylic groups (i.e., carbon-carbon double bonds), halides (i.e., Cl, Br, F, and I), carboxylic acids, esters, activated esters, and the like} that can react to form bonds with other molecules. Generally, each polymerizable monomer molecule can bond to two or more other molecules. In some cases, a polymerizable monomer will bond to only one other molecule, forming a terminus of the polymeric material. Some polymers contain biodegradable linkages, such as esters or amides, such that they can degrade overtime under biological conditions (e.g., at a certain pH present in vivo or in the presence of enzymes).

A "copolymer" refers to a polymer derived from more than one species of monomer. Each species of monomer provides a different species of monomer unit.

As used herein, a "random copolymer" refers to a copolymer wherein the different species of monomer units are arranged in any order. In some embodiments, the random copolymer monomer units are arranged in an order that has no recognizable pattern. The ratio of one monomer unit to another can depend upon a number of factors, e.g., the reactivity of the different monomers and/or other polymerization conditions (e.g., temperature, relative amounts of starting materials, the order of starting material addition, solvent, etc.).

As used herein, a "block copolymer" refers to a copolymer that comprises blocks (i.e., polymeric sub-sections of the whole copolymer) in a linear sequence. A "block" refers to a portion of a copolymer that has at least one feature that is not present in the adjacent portions of the macromolecule. Thus, a "block copolymer" can refer to a copolymer in which adjacent blocks are constitutionally different, i.e., each of these blocks comprises constitutional units derived from different characteristic species of monomer or with different composition or sequence distribution of constitutional units.

For example, a diblock copolymer of PEG and polyserine can be referred to as PEG-block-polyserine. Such a copolymer can also be referred to generically as an "AB block copolymer." Likewise, a triblock copolymer can be represented as "ABA." Other types of block polymers exist, such as multiblock copolymers of the $(AB)_n$ type, ABC block polymers comprising three different blocks, and star block polymers, which have a central point with three or more arms, each of which is in the form of a block copolymer, usually of the AB type.

A "chain" refers to the whole or part of a macromolecule, an oligomer, or a block comprising a linear or branched sequence of constitutional units between two boundary constitutional units, wherein the two boundary constitutional units can comprise an end group, a branch point, or combinations thereof.

A "main chain" or "backbone" of a polymer refers to a linear chain from which all other chains are regarded as being pendant.

A "side chain" or "pendant group" as used herein refers to a monovalent chemical moiety that is attached to the backbone of a polymer chain. The monovalent chemical moiety can comprise an oligomeric or polymeric chain. In some embodiments, the side chain or pendant group is not oligomeric or polymeric.

An "end group" refers to a constitutional unit that comprises the extremity of a macromolecule or oligomer and, by definition, is attached to only one constitutional unit of a macromolecule or oligomer.

Polydispersity (PDI) refers to the ratio ($M_w/M_n$) of a polymer sample. $M_w$ refers to the mass average molar mass (also commonly referred to as weight average molecular weight). $M_n$ refers number average molar mass (also commonly referred to as number average molecular weight).

"Biocompatible" as used herein, generally refers to a material and any metabolites or degradation products thereof that are generally non-toxic to the recipient and do not cause any significant adverse effects to the recipient. Biocompatible polymers include, but are not limited to polyamino acids, such as polyglutamic acid; synthetic block copolymers, such as poloxamers; and polysaccharides, such as glucosaminoglycans.

"Biodegradable" as used herein, generally refers to a material that will degrade or erode under physiologic conditions to smaller units or chemical species that are capable of being metabolized, eliminated, or excreted by the subject. In some embodiments, the degradation time is a function of polymer composition and morphology. Suitable degradation times are from days to weeks. For example, in some embodiments, the polymer can degrade over a time period from seven days to 24 weeks, optionally seven days to twelve weeks, optionally from seven days to six weeks, or further optionally from seven days to three weeks.

The term "hydrophilic" can refer to a group that dissolves or preferentially dissolves in water and/or aqueous solutions.

The term "hydrophobic" refers to groups that do not significantly dissolve in water and/or aqueous solutions and/or which preferentially dissolve in fats and/or non-aqueous solutions.

The term "amphiphilic" refers to a molecule or polymer that contains both hydrophilic and hydrophobic groups.

The terms "conjugate" and "conjugated" can refer to compositions that comprise at least two different chemical moieties or molecules (e.g., small molecules, polymers, proteins, oligonucleotides, etc.) bonded to one another, such as via ionic, coordinative or covalent bonds. Typically, a "conjugate" refers to a situation where the two entities are bonded via a single bond or linkage. In some embodiments, the term "conjugate" refers to moieties or molecules that are covalently bonded to one another.

In some embodiments, the term "complex" refers to compositions that comprise at least two different chemical moieties that are associated with one another via coordinative bonding, ionic bonding, or intermolecular forces such as hydrogen bonding, London dispersion forces, van der Waals' interactions, etc. In some embodiments, the term complex refers to a composition where two entities are associated with one another via electrostatic interactions.

The term "insulin" as used herein refers to insulin from a human or other mammal. In some embodiments, the term "insulin" refers to human insulin. In some embodiments, the term "insulin" refers to recombinant human insulin.

"Bioactive derivative" as used herein in reference to insulin refers to insulin (e.g., human insulin or another mammalian insulin) in which one or more amino acid residues have been replaced by another amino acid residue or deleted, in which the A chain and/or the B chain of the insulin has been extended by addition of one or more amino acid residues at the N-terminal or at the C-terminal, and/or in which the insulin has been modified by the addition of one or more chemical substituents. The derivative can function to replace endogenous insulin and retains at least some of the biological activity of endogenous insulin. Bioactive derivatives can have different pharmacokinetics than endogenous peptides or proteins. Dosages can be optimized based on the pharmacokinetics of the derivative relative to human insulin or human glucagon based on known pharmacokinetics by one of skill in the art.

The term "diabetes treatment agent" as used herein can refer to a therapeutic agent that treats diabetes or a complication thereof (such as, but not limited to, diabetic neuropathy, diabetic retinopathy, diabetic nephropathy, glaucoma, and diabetic ketoacidosis) or another glucose metabolism disorder that results in hyperglycemia. In some embodiments, the diabetes treatment agent is an insulin or a bioactive derivative thereof or a non-insulin-based treatment agent known in the art for use in the treatment of diabetes. Suitable non-insulin-based treatment agents for use in the treatment of diabetes include, but are not limited to, insulin sensitizers, DPP IV inhibitors, glucagon-like peptide 1 (GLP-1) and analogs thereof, insulin secretagogues, such as, but not limited to sulfonylureas, meglitinides, gastric inhibitory polypeptide (GIP), insulin receptor activators, biguanides, thiazolidinediones, alpha-glucosidase inhibitors, and the like. In some embodiments, the diabetes treatment agent is an insulin or a bioactive derivative.

The terms "cross-linking reagent" or "cross-linking agent" refer to a compound that includes at least two reactive functional groups (or groups that can be deblocked or deprotected to provide reactive functional groups), which can be the same or different. In some embodiments, the two reactive functional groups can have different chemical reactivity (e.g., the two reactive functional groups are reactive (e.g., form bonds, such as covalent bonds) with different types of functional groups on other molecules, or one of the two reactive functional groups tends to react more quickly with a particular functional group on another molecule than the other reactive functional group). Thus, the cross-linking reagent can be used to link (e.g., covalently bond) two other entities (e.g., molecules, polymers, proteins, nucleic acids, vesicles, liposomes, nanoparticles, microparticles, etc.) of to link two groups on the same entity (e.g., a polymer) to form a cross-linked composition. Generally, as used herein, the term "cross-linked" refers to a composition comprising multiple bonds or linkages between two entities or comprising multiple added bonds or linkages between groups on the same entity.

The term "hyperglycemia", as used herein, can refer to a condition in which an elevated amount of glucose circulates in the blood plasma of a subject relative to a healthy individual. Hyperglycemia can be diagnosed using methods known in the art, including measurement of fasting blood glucose levels.

The term "hypoglycemia", as used herein, can refer to a condition in which a reduced amount of glucose circulates in the blood plasma of a subject. The reduced level of glucose that can signify hypoglycemia can vary depending upon the age and health of a subject. For a diabetic adult, a blood glucose level of 70 mg/dL or less can be referred to as hypoglycemia. For a non-diabetic adult, a blood glucose level of 50 mg/dL or less can be referred to as hypoglycemia. Hypoglycemia can be diagnosed using methods known in the art, including via the use of a commercially available fingerstick blood glucose monitors, continuous blood glucose monitors, measuring venous blood glucose levels, etc. Symptoms of hypoglycemia include, but are not limited to, jitters, blurred vision, sweating, pallor, personality changes, headaches, weakness, hunger, sleepiness, nausea, dizziness, trouble concentrating, irregular heartbeat, confusion, seizures, and coma.

In some embodiments, the hypoglycemia can be related to an elevated level of insulin circulating in the blood, i.e., hyperinsulinemic hypoglycemia. In some embodiments, the hyperinsulinemic hypoglycemia can be the result of the treatment of type 1 or type 2 diabetes with insulin replacement therapy (e.g., insulin injection) and/or with another diabetic treatment agent, e.g., a sulfonylurea or a meglitinide. Thus, in some embodiments, the hypoglycemia can be caused by an excess of injected insulin. In some embodiments, the hypoglycemia can be caused by an excess of endogenous insulin. In some embodiments, the hyperinsulinemic hypoglycemia can be caused by, for example, congenital hyperinsulinism, an insulinoma (e.g., an islet cell adenoma or carcinoma), gastric dumping syndrome, autoimmune insulin syndrome, reactive hypoglycemia, or non-insulinoma pancreatogeneous hypoglucemia. In some embodiments, the use of certain drugs, such as, but not limited to sulfonylureas, meglitinides, aspirin, pentamide, quinine, or disoperamide, can result in hypoglycemia.

The term "insulin resistance" as used herein can refer to a condition where a normal amount of insulin is unable to produce a normal physiological or molecular response. In some cases, a hyper-physiological amount of insulin, either endogenously produced or exogenously administered, is able to overcome the insulin resistance, in whole or in part, and produce a biologic response.

The term "metabolic syndrome" as used herein can refer to an associated cluster of traits that includes, but is not limited to, hyperinsulinemia, abnormal glucose tolerance, obesity, redistribution of fat to the abdominal or upper body compartment, hypertension, dysfibrinolysis, and dyslipidemia characterized by high triglycerides, low high density lipoprotein (HDL)-cholesterol, and high small dense low density lipoprotein (LDL) particles. Subjects having metabolic syndrome are at risk for development of Type 2 diabetes and/or other disorders (e.g., atherosclerosis).

The term "glucose tolerance," as used herein, can refer to the ability of a subject to control the level of plasma glucose and/or plasma insulin when glucose intake fluctuates. For example, glucose tolerance encompasses the ability to reduce the level of plasma glucose back to a level before the intake of glucose within about 120 minutes or so.

As used herein, a "polysaccharide" is a polymer of sugars. The terms "polysaccharide", "carbohydrate", and "oligosaccharide", may be used interchangeably. The polymer can include natural sugars (e.g., glucose, fructose, galactose, mannose, arabinose, ribose, and xylose) and/or modified sugars (e.g., 2'-fluororibose, 2'-deoxyribose, and hexose).

As used herein, the term "saccharide" refers to monomers of sugars. A saccharide can be a natural sugar (e.g., glucose, fructose, galactose, mannose, arabinose, ribose, and xylose) or a modified sugar (e.g., 2'-fluororibose, 2'-deoxyribose, hexose, etc.).

II. General Considerations

Significant efforts have been devoted to the development of self-regulated, glucose-responsive insulin delivery systems. See Lu et al., Nat. Rev. Mater., 2017, 2, 1-17. The majority of these systems have involved the use of the interaction of glucose with glucose oxidase (GOx) (see Ito et al., J. Control. Release, 1989, 10, 195-203; Gordio et al., Adv. Funct. Mater., 2011, 21, 73-82; Podual et al., J. Control Release, 2000, 67, 9-17; and Podual et al., Annu. Rev. Biomed. Eng., 2000, 2, 9-29), glucose-binding protein (see Brownlee and Cerami, Science, 1979, 206, 1190-1191; Brownlee and Cerami, Diabetes, 1983, 32, 499-504; Obaidat and Park, Pharm. Res., 1996, 13, 989-995; and Wanq et al., Adv. Mater., 2017, 29, 1606617), or phenylboronic acid (PBA). See Donq et al., Langmuir, 2016, 32, 8743-8747; Chou et al., Proc. Natl. Acad. Sci. USA, 2015, 112, 2401-2406; Matsumoto et al., Macromolecules, 2004, 37, 1502-1510; Shiino et al., J. Control Release, 1995, 37, 269-276; Matsumoto et al., Biomacromolecules, 2004, 5, 1038-1045; Kataoka et al., J. Am. Chem. Soc., 1998, 120, 12694-12695; and Brooks and Sumerlin, Chem. Rev., 2016, 116, 1375-1397. For example, PBA can reversible bind 1,2- or 1,3-cis-diols (see Springsteen and Wanq, Tetrahedron, 2002, 58, 5291-5300; and Yan et al., Tetrahedron, 2004, 60, 11205-11209), resulting in enhanced water solubility and subsequent payload release through swelling (see Matsumoto et al., Angew. Chem. Int. Edit., 2012, 51, 2124-2128), dissolving (see Kim et al., ACS Macro Letters, 2012, 1, 1194-1198), or viscosity-thinning of carriers (see Yao et al., Biomacromolecules, 2012, 13, 1837-1844; Ma et al., Biomacromolecules, 2102, 13, 3409-3417; and Yang et al., Soft Matter, 2013, 9, 8589-8599) under a hyperglycemic state. However, these systems still face several challenges, including slow response rate, low insulin loading efficiency, poor biocompatibility, and complicated manipulation processes. See Lu et al., Nat. Rev. Mater., 2017, 2, 1-17.

The presently disclosed subject matter relates, in some embodiments, to compositions for the delivery of insulin (or bioactive derivatives thereof) to a subject in need thereof, e.g., for the control of diabetes or another glucose metabolism disorder that leads to hyperglycemia. It could also be useful for delivering other negatively charged protein and small molecule therapeutic agents, such as anticancer/anti-inflammation drugs and/or other drugs (such as a diabetes treatment agent as disclosed herein) to treat diabetes and/or hyperglycemia and/or the side effects thereof. In particular, in some embodiments, the presently disclosed compositions can provide glucose-sensitive, "smart", closed-loop insulin delivery to a subject in need thereof, thereby providing for more cost-effective and easier control of diabetes, to improve health and life-quality of diabetic patients, as well as to prevent hypoglycemic complications of the treatment of diabetes.

More particularly, the presently disclosed subject matter is based on an electrostatic interaction-driven complex formed between a negatively charged therapeutic agent, e.g., insulin (or a bioactive derivative thereof), and a charge-switchable polymer comprising a glucose-sensing moiety and a positively charged moiety. In the presence of glucose, the glucose-sensing moiety can rapidly or instantaneously bind to glucose and introduce negative charge into the polymer, thereby reducing the amount of positive charge in the polymer, which provides for the release of the negatively charged therapeutic agent, e.g., the insulin (or its bioactive derivative), from the complex. By rationally adjusting the ratio between the positively charged moiety of the polymer and the glucose sensing moiety, the therapeutic agent can be slowly released from the complex under normoglycemia, but quickly (e.g., instantly) released under hyperglycemia. As an example, using an insulin-polymer complex of the presently disclosed subject matter, in vivo glucose-responsive insulin release was achieved upon glucose challenge, with the complex tightly regulating blood glucose levels in mouse and minipig models of type I diabetes.

Figure 1A:
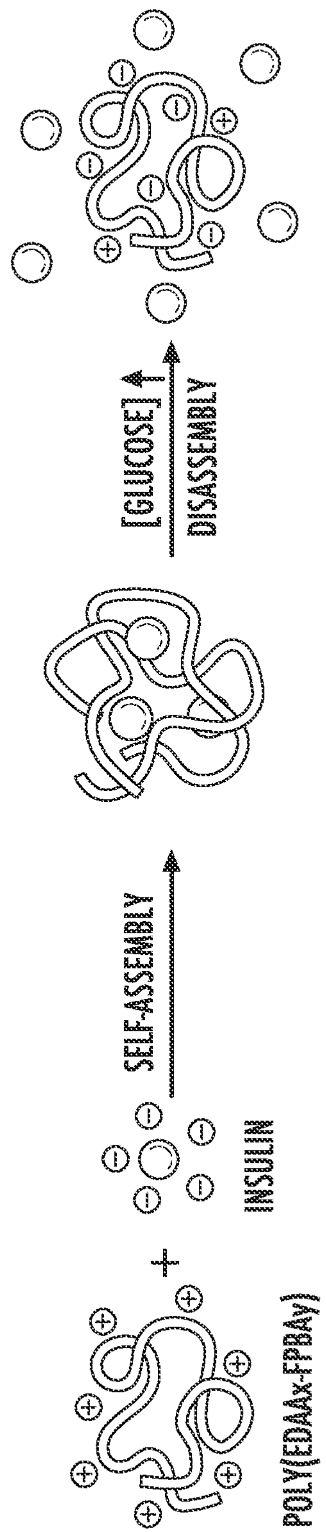
FIG. 1A is schematic drawing of a glucose-responsive insulin delivery system of the presently disclosed subject matter. On the left, a positively charged polymer (e.g., a poly(ethylene diamine acrylamide) (poly(EDAA)) where some of the pendent amino groups are grafted to fluorophenyl boronic acid (FPBA) groups (i.e., poly($EDAA_x$-$FPBA_y$))) is mixed with insulin, which is negatively charged. The polymer and insulin mixture self-assembles into an insulin-polymer complex (middle) via electrostatic interaction. Upon exposure to glucose (left), e.g., in a hypoglycemic state, the number of positive charges of the polymer are reduced and insulin is released as the insulin-polymer complex disassembles.
Figure 1B:
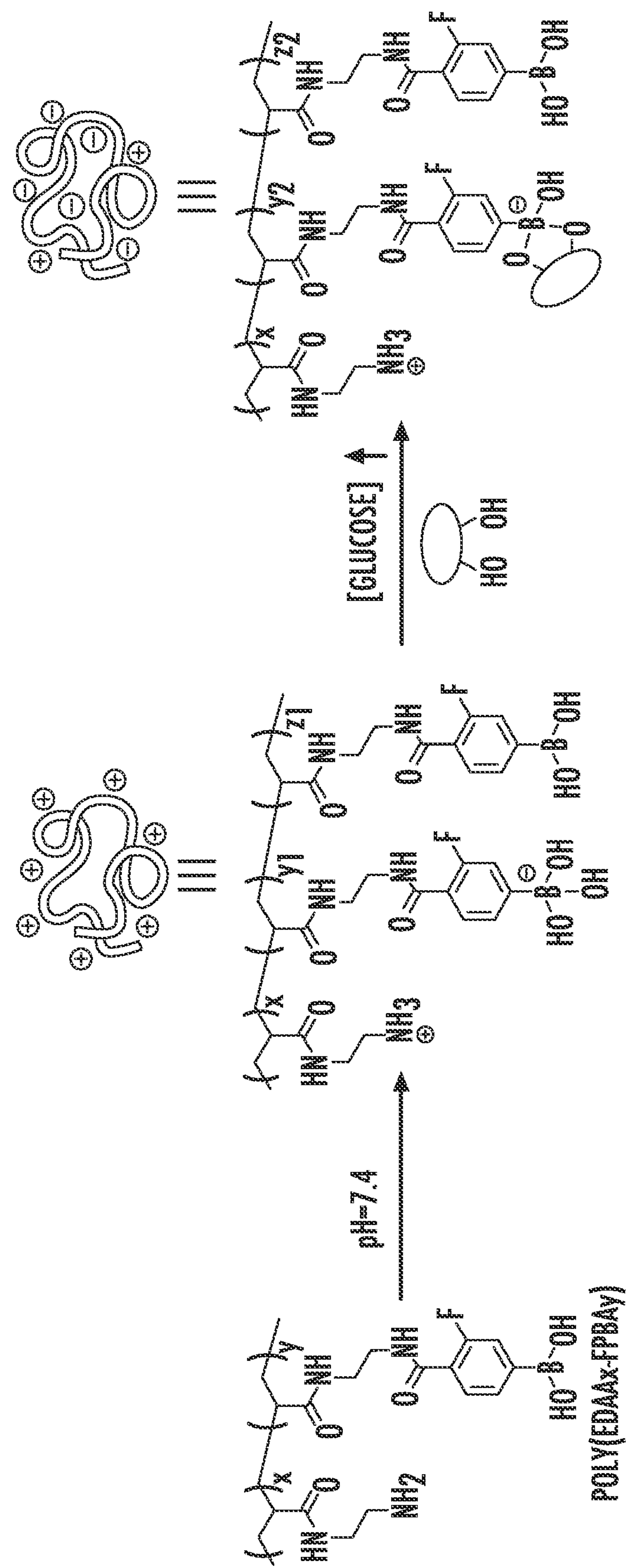
FIG. 1B is a schematic drawing showing additional details of the structure of the polymer described above in FIG. 1A, both before (middle) and after (right) glucose binding to the fluorophenylboronic acid groups of the polymer side chains.

An exemplary embodiment of the presently disclosed subject matter is shown in FIGS. 1A and 1B. As shown in FIG. 1B, a positively-charged polymer (i.e., poly(ethylene diamine acrylamide) (poly(EDAA) or poly(2-aminoethyl-acrylamide)) is incorporated with pendant amine groups, some of which are further conjugated to a fluorophenyl boronic acid (FPBA) group. In phosphate buffer solution (PBS) without glucose at pH 7.4, this polymer is positively charged (see FIGS. 1A and 1B) and able to form a stable micro-sized complicated suspension with insulin (see FIG. 1A) with an impressive insulin loading efficiency as high as 95%. In the presence of glucose, the binding of glucose to FPBA groups in the polymer leads to a gradual decrease of positive charge, thereby weakening the electrostatic interaction between the polymer and insulin. Under a hyperglycemic condition, the positive charges of the polymer can be reversed highly and quickly, therefore facilitating insulin release with fast response. See FIG. 1A, right. However, such charge-reversal is inhibited under a normoglycemic state, therefore reducing the insulin release rate and subsequently avoiding the risk of hypoglycemia.

In some embodiments, the presently disclosed complexes are formed rapidly by mixing the therapeutic agent (e.g., the insulin or bioactive derivative thereof) with a polymer. Almost 100% (e.g., more than 90, 95, 98, or 99%) of the agent can become complexed with the polymer. Thus, further purification is not needed. Under hyperglycemic conditions, the polymer can rapidly bind to glucose, introducing negative charges and leading to significant reduction in the positive charge of the polymer. The process is very rapid, and therapeutic agent (e.g., insulin) can be released to respond to a change in blood glucose level. It is believed that the presently disclosed complexes are the first to use the negative charge carried on an arylboronic acid (e.g., a halophenylboronic acid) after binding to glucose to achieve glucose-dependent insulin release. A fast and sharp responsiveness to glucose level was observed in both in vitro and in vivo studies.

According to the presently disclosed subject matter, the delivery system comprises two components (e.g., a polymer and insulin) that are highly biocompatible. In addition, compared to other, more complicated glucose-responsive delivery methods, which can contain a significant amount of pharmaceutic adjuvant, the amount of polymer in the presently disclosed complexes is at a relatively low level due to the high loading content. For instance, complexes of polymer and insulin can comprise about 50 weight (wt) % insulin, therefore reducing potential biocompatibility concerns associated with more complicated glucose-responsive insulin delivery methods/systems.

The presently disclosed subject matter can also offer more patient-friendly administration. As an example, diabetic patients typically are administered three injections of rapid-acting insulin and one injection of long-acting insulin. However, only a single dose was needed to maintain normoglycemia for an entire day using the presently disclosed glucose-responsive insulin-polymer complexes. Thus, the presently disclosed complexes can significantly reduce the number of injections a patient needs (e.g., to control blood glucose levels effectively), elevating administration convenience and making treatment more acceptable to patients.

In some embodiments, the presently disclosed subject matter provides a composition comprising (a) a positively-charged polymer comprising glucose-binding groups and (b) insulin or a bioactive derivative thereof. In some embodiments, the positively charged polymer comprises ammonium groups (e.g., ammonium groups formed from the protonation of amine groups at biologically relevant pH, e.g., a pH of about 7.4 or less). The positively charged polymer and the insulin or bioactive derivative thereof can form a complex via electrostatic interactions.

The term "glucose-binding group" as used herein refers to a group that binds (e.g. via covalent, coordinative, or non-covalent bonds) to glucose or another vicinal diol, such as another sugar or a polysaccharide. In some embodiments, the glucose-binding group can bind reversibly to glucose or another sugar or polysaccharide. In some embodiments, the glucose-binding group is a group that can undergo a change in electric charge or charge density upon binding to glucose or another sugar or polysaccharide. Suitable glucose-binding groups include, but are not limited to, monosaccharide binding proteins, such as glucose binding protein (GBP) (also known as galactose/glucose binding protein) and derivatives thereof, glucose transporter proteins (e.g., GLUT1-14) and derivatives thereof, and boronic acids and boronic acid esters. For instance, the reversible complexation of a saccharide with an aromatic boronic acid can produce a stable boronate anion. In some embodiments, the glucose-binding group comprises a boronic acid or a boronic acid ester. In some embodiments, the glucose-binding group comprises an arylboronic acid or arylboronic acid ester group. The aryl portion of the arylboronic acid or arylboronic acid ester can be for example, phenyl, naphthyl, anthracenyl, biphenyl, pyrenyl, a heteroaryl group, or a substituted aromatic or heteroaryl group.

In some embodiments, the arylboronic acid group is a phenylboronic acid group, which can be substituted or unsubstituted with one or more aryl group substituents (e.g., halo, alkyl, alkoxy, etc.). In some embodiments, the arylboronic acid group is a halophenylboronic acid group. In some embodiments, the phenylboronic acid group is a fluorophenylboronic acid group.

In some embodiments, the insulin or bioactive derivative thereof can be human insulin, recombinant human insulin, insulin from a non-human animal source (e.g. bovine, porcine) or any other insulin, including insulin derivatives. In some embodiments, the insulin is of the same species as the intended recipient, i.e., human insulin for treatment of humans. The insulin or bioactive derivative thereof can include mixtures of different insulins and/or derivatives. The insulin or bioactive derivative thereof can include fast-acting insulins, rapid-acting insulin analogs, intermediate-acting insulins, and/or long-acting insulins. In some embodiments, the insulin or bioactive derivative thereof is a fast-acting or rapid-acting insulin. In some embodiments, the insulin or bioactive derivative thereof is recombinant human insulin.

Fast-acting insulins start to work within one to 20 minutes, peaking about one hour later and lasting from three to five hours. Fast-acting insulin takes about two hours to fully absorb into the systemic circulation. Fast-acting insulins include regular recombinant human insulin (such as HUMULIN™ marketed by Lilly, and NOVOLIN™, marketed by NovoNordisk). Bovine and porcine insulins, which differ in several amino acids to human insulin, but are bioactive in humans, are also fast acting insulins.

Rapid-acting insulins include insulins that have been modified or have altered locations of amino acids in order to enhance their rate of absorption. There are three types of rapid-acting commercial insulin analogs available: lispro insulin (Lysine-Proline insulin, sold by Eli Lilly as HUMALOG™), glulisine insulin (sold by Sanofi-Aventis as APIDRA™) and as part insulin (sold by Novo Nordisk as NOVOLOG™).

Intermediate-acting insulin has a longer lifespan than short-acting insulin, but it is slower to start working and takes longer to reach its maximum strength. Intermediate-acting insulin usually starts working within 2-4 hours after injection, peaks somewhere between 4-14 hours and remains effective up to 24 hours. Types of intermediate-acting insulin include NPH (Neutral Protamine Hagedorn) and LENTE™ insulin. NPH insulin contains protamine which slows down the speed of absorption so that the insulin takes longer to reach the bloodstream but has a longer peak and lifespan.

Long-acting insulins include Eli Lilly's Humulin™ U (Ultralente™ human insulin (recombinant DNA origin) extended zinc suspension); and insulin glargine (LANTUS™ Aventis). Insulin glargine is a recombinant human insulin analog that can have up to 24 hour duration. It differs from human insulin by having a glycine instead of asparagine at position 21 and two arginines added to the carboxy-terminus of the beta-chain. LANTUS™ consists of insulin glargine dissolved in a clear aqueous fluid (100 IU, 3.6378 mg insulin glargine, 30 micrograms zinc, 2.7 mg m-cresol, 20 mg glycerol 85%, and water to 1 ml).

In some embodiments, some or all of the insulin or bioactive derivative thereof can be replaced by another negatively charged therapeutic protein, peptide or other agent. In some embodiments, the composition can also include another diabetes treatment agent.

In some embodiments, the positively charged polymer comprises a vinyl copolymer (e.g., a random vinyl copolymer), although other polymer backbones (e.g., polyamides) can also be used. In some embodiments, the copolymer has a plurality of side chains wherein one or more of the side chains comprise an ammonium group and wherein one or more side chains comprises a glucose binding group. In some embodiments, the polymer can be formed from monomeric units comprising N-substituted acrylamides. In some embodiments, some of the monomeric units can be derived from an N-substituted acrylamide substituted with an aminoalkyl group. In some embodiments, the aminoalkyl substituted acrylamide is the product of a reaction between acryloyl chloride (or another acryloyl halide or acrylic acid or an ester or anhydride thereof) and a diamine, such as ethylene diamine or a propylene diamine (i.e., 1,3-diaminopropane or 1,2-diaminopropane) or a mono-protected diamine. Suitable amino protecting groups (e.g., tert-butoxycarbonyl or Boc) are known in the art. In some embodiments, the polymer can be a copolymer of monomeric units comprising a side chain comprising a protonated amine (e.g., a protonated primary amine) and monomeric units comprising a side chain containing a glucose-binding group, such as an arylboronic acid or arylboronic acid ester moiety.

In some embodiments, the copolymer has a polyacrylamide backbone comprising a plurality of side chains comprising an ammonium group and a plurality of side chains comprising a glucose-binding group. In some embodiments, the polymer has a structure of formula (I):

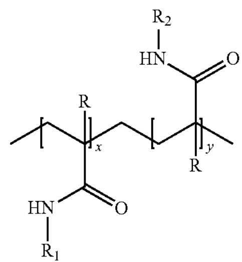

wherein:

x and y are each integers greater than 1;

R is H or alkyl;

$R_1$ is a protonated aminoalkyl group; and $R_2$ is a group comprising an arylboronic acid.

In some embodiments, each of x and y are integers greater than about 10, 15, 20, 25, 30, 35, 40, 45, 50, 75, or 100. In some embodiments, x and y are each independently an integer between about 50 and about 5,000 (e.g., 50; 75; 100; 200; 300; 400; 500; 600; 700; 800; 900; 1,000; 1,500; 2,000; 2,500; 3,000; 4,000; or 5,000). In some embodiments, x and y can be integers greater than about 5,000; 10,000; 25,000; or more. In some embodiments, the sum of the integers x and y is at least about 10, 20, 30, 40, 50, 60, 70, 80, 90, or about 100. In some embodiments the sum of x and y is about 500; 1,000; 5,000; 10,000; 25,000; 50,000, or more.

In some embodiments, the ratio of x to y is between about 7:3 and about 1:5 (e.g., about 7:3, 2:1, 5:3, 4:3, 1:1, 2:3, 1:2, 1:3, 1:4, or 1:5). In some embodiments, the ratio of x to y is about 1:1 to about 1:3. In some embodiments, the ratio of x to y is about 2:3.

In some embodiments, R is H or $C_1$-$C_6$ alkyl, such as methyl, ethyl, propyl, isopropyl, n-butyl, iso-butyl, sec-butyl, tert-butyl, pentyl (e.g., n-pentyl or neo-pentyl), or hexyl. In some embodiments, R is H or methyl. In some embodiments, R is H.

In some embodiments, $R_1$ has the structure $-L-NH_3^+$, wherein L is a $C_1$-$C_6$ straight or branched, substituted or unsubstituted alkylene group. In some embodiments, L is ethylene, i.e., $—CH_2CH_2—$.

In some embodiments, $R_2$ has the structure $-L_1-NH—C(=O)—R_3$, wherein $L_1$ is a $C_1$-$C_6$ straight or branched, substituted or unsubstituted alkylene group, wherein $R_3$ is an arylboronic acid group. In some embodiments, $R_3$ is a phenylboronic acid group. In some embodiments, $R_3$ is a fluorophenylboronic acid group or another halophenylboronic acid group. In some embodiments, L and $L_1$ are the same. In some embodiments, $L_1$ is $—CH_2CH_2—$.

In some embodiments, the composition comprises a weight ratio of positively charged polymer to insulin (or bioactive derivative thereof) of between about 2:1 and about 1:4 (e.g., about 2:1, about 1.5:1; about 1:1; about 1:1.5; about 1:2; about 1:3; or about 1:4). In some embodiments, the composition comprises about equal amounts (by weight) of polymer and insulin (or bioactive insulin derivative), and the ratio is about 1:1.

In some embodiments, the composition forms a nano- or microparticle comprising the polymer and the insulin (or bioactive derivative thereof). In some embodiments, the nano- or microparticle has an approximately spherical shape. In some embodiments, the nano- or microparticle has an irregular shape. In some embodiments, the nano- or microparticle has a diameter of between about 0.1 micrometers (μm) and about 1000 μm. In some embodiments, the particle has a diameter of between about 1 μm and about 200 μm (e.g., about 1, 5, 10, 20, 30, 40, 50, 60, 70, 80, 90, 100, 110, 120, 130, 140, 150, 160, 170, 180, 190, or about 200 μm). In some embodiments, the particle has a diameter of about 50 μm.

In some embodiments, the compositions of the presently disclosed subject matter, e.g., the nano- and/or microparticles, can be used to prepare microneedle (MN) arrays for the delivery of insulin or a bioactive derivative thereof. For example, in some embodiments, the presently disclosed subject matter provides a microneedle array comprising a plurality of microneedles comprising nano- and/or microparticles, wherein the particles comprise a complex between a positively-charged polymer and insulin, wherein the positively charged polymer comprises glucose-binding groups. In some embodiments, the microneedle array can comprise a plurality of microneedles wherein each of said plurality of microneedles has a length of between about 20 and about 1000 microns (e.g., about 20, 50, 100, 150, 200, 250, 300, 350, 400, 450, 500, 550, 600, 650, 700, 750, 800, 850, 900, 950, or about 1000 microns). In some embodiments, each of the plurality of microneedles has a length of between about 500 microns and about 700 microns. In some embodiments, each microneedle can have an approximately conical or pyramidal shape. In some embodiments, the tip of the microneedles can be less than about 100 microns, less than about 75 microns, less than about 50 microns, less than about 40 microns, less than about 30 microns, or less than about 20 microns. In some embodiments, the tip of each of the microneedles can be about 10 microns.

The microneedle array can comprise a plurality of microneedles, wherein the bases of microneedles are arranged in any suitable two-dimensional pattern. The microneedles can be arranged in a regular array (e.g., a square, rectangular, circular, oval or other shaped pattern) wherein the distance between individual microneedles remains the same or varies in a repeating fashion, or in an irregular array (e.g., wherein the distance between individual microneedles varies in no recognizable repeating fashion). The microneedles can be prepared by dropping a solution comprising the presently disclosed complex (e.g., nanoparticles of an insulin/polymer complex) into a mold and adding a solution comprising a cross-linkable biocompatible polymer, such as, but not limited to a cross-linkable polyamino acid (e.g., polyglutamic acid), a cross-linkable synthetic block copolymer or a cross-linkable polysaccharide (e.g., a glucosaminoglycan). In some embodiments, the cross-linkable biocompatible polymer is acrylate-modified hyaluoric acid (m-HA). Then the mold can be dried and the cross-linkable polymer can be cross-linked (e.g., using N,N'-methylene bisacrylamide (MBA) or another crosslinking agent). Afterward, the microneedles can be removed from the mold.

FIG. 6 shows a schematic diagram of an exemplary method for preparing a microneedle array of the presently disclosed subject matter. A solution comprising a composition comprising an insulin-polymer complexes (e.g., nanoparticles prepared from an insulin-polymer complex of the presently disclosed subject matter) is dropped into a silicone mold comprising a plurality of microcavities (e.g., using a micropipette). The solution can also optionally comprise a cross-linkable biocompatible polymer, a crosslinking agent and a photoinitiator. The filled mold is centrifuged to eliminate any remaining air from the microcavities. The dropping and centrifuging steps can be repeated one or more times (e.g., one, two, three or more times), as needed, to fill the microcavities. Then, the filled mold is dried, e.g., under vacuum conditions. After drying, a cross-linkable biocompatible polymer solution (e.g., a m-HA solution), optionally comprising a crosslinking agent or a crosslinking agent and a photoinitiator, is dropped onto the mold and dried, forming a polymer layer over the top of the filled microcavities. Then the resulting dried MN patch is detached from the mold and exposed to UV radiation of a period of time to initiate crosslinking of the polymer(s).

In some embodiments, the microneedle array can be provided as part of a skin patch. In some embodiments, the microneedle array can comprise one or more backing layers (e.g., to protect the microneedle array from moisture or physical insult (e.g., scratches). In some embodiments, the microneedle array can comprise a layer that extends outward from the array (e.g., coplanar to the base of the array) that comprises a skin-compatible adhesive for aiding in the attachment of the array to the skin.

The presently disclosed microneedle arrays can release insulin or a bioactive derivative thereof in a glucose-responsive or dependent manner. In some embodiments, the release rate of the insulin or bioactive derivative is directly dependent upon the concentration of glucose coming into contact with the array (e.g., the release rate is faster when the array is in contact with higher concentrations of glucose). Thus, in some embodiments, the microneedle array is a closed-loop insulin delivery system.

In some embodiments, the presently disclosed subject matter provides a pharmaceutical formulation comprising a pharmaceutically acceptable carrier and a composition comprising a complex between a positively-charged polymer and insulin or a bioactive derivative thereof, wherein the positively-charged polymer comprises a glucose-binding group. In some embodiments, the complex is in the form of a nano- or microparticle. In some embodiments, the carrier can be a pharmaceutically acceptable liquid or a biocompatible polymer (e.g., a hydrophobic or amphiphilic polymer gel). In some embodiments, the carrier is a poloxamer, i.e., a triblock copolymer comprising a central hydrophobic poly(propylene glycol) (PPG)) block flanked by two hydrophilic poly(ethylene glycol) (PEG) blocks, such as, but not limited to PF-127.

As used herein, the term "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the liposomal pharmaceutical compositions. The presently disclosed compositions can be lyophilized to produce a lyophilizate, which can be reconstituted with a pharmaceutically acceptable carrier, such as water, to regenerate a suspension or solution.

A pharmaceutical composition can be formulated to be compatible with its intended route of administration. Examples of routes of administration include, but are not limited to, parenteral, intravenous, intradermal, subcutaneous, oral (e.g., inhalation), transdermal (topical), transmucosal, nasal, optical, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

In some embodiments, the presently disclosed subject matter provides a method of delivering insulin or a bioactive derivative thereof to a subject in need thereof, the method comprising administering a skin patch or a pharmaceutical formulation comprising the presently disclosed polymer complex.

In some embodiments, the subject treated according to the presently disclosed subject matter is a human subject, although it is to be understood that the methods described herein are effective with respect to all vertebrate species, which are intended to be included in the term "subject."

More particularly, provided herein is the treatment of mammals, such as humans, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Thus, embodiments of the methods described herein include the treatment of livestock, including, but not limited to, domesticated swine (pigs and hogs), ruminants, horses, poultry, and the like.

In some embodiments, the subject is diabetic. The subject can have type 1 or type 2 diabetes. In some embodiments, the subject has a metabolic disorder. In some embodiments, the subject is a mammal. In some embodiments, the subject is a human.

In some embodiments, the administering comprises administering the pharmaceutical formulation via subcutaneous injection. In some embodiments, the administration is performed once a day. In some embodiments, the pharmaceutical formulation or patch releases insulin at a rate that corresponds directly to the blood glucose levels of the subject (e.g., such that when the subject has normoglycemia, release is slow, but when the subject has hyperglycemia, release is rapid). Thus, the presently disclosed complex can act as a depot to release insulin over the course of several hours or days as needed.

In some embodiments, the presently disclosed subject matter provides a method of treating diabetes in a subject in need thereof, wherein the method comprises administering a pharmaceutical formulation comprising a complex as described herein or a skin patch comprising microneedles comprising the complex. The subject can have type 1 or type 2 diabetes. In some embodiments, the administering comprises administering the pharmaceutical formulation via subcutaneous injection. In some embodiments, the administration is performed once a day. In some embodiments, administration can be performed more than once a day (e.g., two or three patches can be applied per day). In some embodiments, the pharmaceutical formulation or patch releases insulin at a rate that corresponds directly to the blood glucose levels of the subject.

In some embodiments, the presently disclosed subject matter provides a polymer that can be used to prepare a glucose-responsive complex with a negatively-charged therapeutic moiety, such as insulin or a bioactive derivative thereof. In some embodiments, the polymer comprises a plurality of side chains wherein some of the side chains comprise a group (e.g., an amine) that is positively charged at biologically relevant pHs (e.g., at or below about 7.4) and wherein some of the side chains comprise a group that can bind to glucose and/or other saccharides. In some embodiments, the polymer is a copolymer (e.g., a random copolymer) comprising monomeric units that comprise a group that can be positively charged at a biologically relevant pH and monomeric units that comprise a glucose-binding group.

In some embodiments, the polymer can be formed from monomeric units comprising N-substituted acrylamides. In some embodiments, some of the monomeric units can be derived from an N-substituted acrylamide substituted with an aminoalkyl group. In some embodiments, the aminoalkyl substituted acrylamide is the product of a reaction between acryloyl chloride (or another acryloyl halide or acrylic acid or an ester or anhydride thereof) and a diamine, such as ethylene diamine or a propylene diamine (i.e., 1,3-diaminopropane or 1,2-diaminopropane) or a mono-protected diamine. Suitable amino protecting groups (e.g., tert-butoxycarbonyl or Boc) are known in the art. In some embodiments, the polymer can be a copolymer of monomeric units comprising a side chain comprising a protonated amine (e.g., a protonated primary amine) and monomeric units comprising a side chain containing a glucose-binding group, such as an arylboronic acid or arylboronic acid ester moiety. In some embodiments, the copolymer can be obtained by reacting a polymer comprising amino group-containing side chains with a reagent that comprises a glucose-binding group under conditions such that only a portion of the amino group-containing side chains react with the reagent and become attached to the glucose-binding group. For example, in some embodiments, the conditions can be varied to provide a desired percentage of remaining amino group-containing side chains by varying the amount of the glucose-binding group-containing reagent.

Accordingly, in some embodiments, the presently disclosed subject matter provides a composition comprising a polyacrylamide polymer comprising pendent aminoalkyl groups and pendant arylboronic acid or arylboronic ester groups. In some embodiments, the aryl group of the arylboronic acid or arylboronic ester group is substituted by one or more aryl group substituent (e.g., a halo, alkyl, alkoxy, etc.). In some embodiments, the arylboronic acid or boronic ester group is a haloarylboronic acid or haloboronic ester group. In some embodiments, the polymer is a polyacrylamide polymer comprising pendent aminoalkyl groups and pendent fluorophenylboronic acid groups.

In some embodiments, the composition comprises a copolymer having a structure of formula (II):

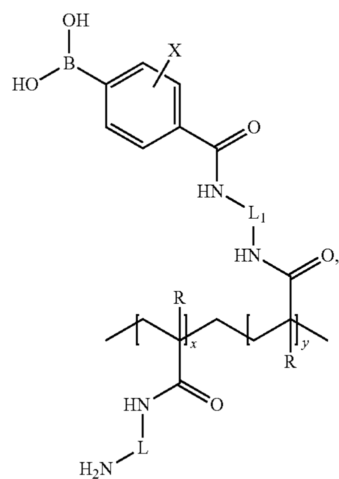

wherein:

x and y are each integers greater than about 5;

R is H or alkyl;

L and $L_1$ are each alkylene; and

X is halo.

In some embodiments, x and y are each integers greater than about 10, 15, 20, 25, 50, 75, 100, 250, 500, 750, 1000, 2500, 5000, 7500, or 10000. In some embodiments, the ratio of x:y is between about 7:3 x:y and about 1:5 x:y (e.g., about 7:3, 2:1, 5:3, 4:3, 1:1, 2:3, 1:2, 1:3, 1:4, or about 1:5). In some embodiments, x:y is about 2:3.

In some embodiments R is H or $C_1$-$C_6$ alkyl, such as methyl, ethyl, propyl, isopropyl, n-butyl, iso-butyl, sec-butyl, tert-butyl, pentyl (e.g., n-pentyl or neo-pentyl), or hexyl. In some embodiments, R is H or methyl. In some embodiments, R is H. In some embodiments, L and $L_1$ are each $C_1$-$C_6$ alkylene. In some embodiments, L and $L_1$ are different alkylene groups. In some embodiments, L and $L_1$ are the same alkylene groups. For example, L and $L_1$ can both be ethylene or propylene. In some embodiments, X is fluoro, chloro or bromo. In some embodiments, X is fluoro. In some embodiments, the primary amine groups are protonated.

In some embodiments, the polymer has a structure of formula (III):

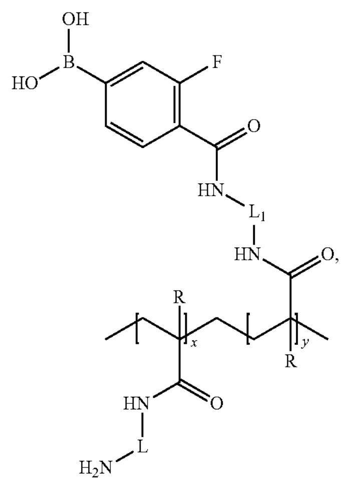

wherein x and y are each integers greater than 5;

R is H or alkyl; and

L and $L_1$ are each alkylene independently selected from $C_1$-$C_5$ alkylene.

In some embodiments, x and y are each integers greater than about 10, 15, 20, 25, 50, 75, 100, 250, 500, 750, 1000, 2500, 5000, 7500, or 10000. In some embodiments, the ratio of x:y is between about 7:3 x:y and about 1:5 x:y (e.g., about 7:3, 2:1, 5:3, 4:3, 1:1, 2:3, 1:2, 1:3, 1:4, or about 1:5). In some embodiments, x:y is about 2:3.

In some embodiments R is H or $C_1$-$C_6$ alkyl, such as methyl, ethyl, propyl, isopropyl, n-butyl, iso-butyl, sec-butyl, tert-butyl, pentyl (e.g., n-pentyl or neo-pentyl), or hexyl. In some embodiments, R is H or methyl. In some embodiments, R is H. In some embodiments, L and $L_1$ are different alkylene groups. In some embodiments, L and $L_1$ are the same alkylene groups. For example, L and $L_1$ can both be ethylene or propylene. In some embodiments, L and/or $L_1$ are ethylene (i.e., —$CH_2CH_2$—). In some embodiments, X is fluoro, chloro or bromo. In some embodiments, X is fluoro. In some embodiments, the primary amine groups are protonated.

The polymer can have any suitable molecular weight (e.g, a mass average molecular weight $M_w$) of between about 1 kilodalton (kDa) and about 30 kDa. Thus, in some embodiments, the polymer has a $M_w$ of about 1, 2.5, 5, 7.5, 10, 12.5, 15, 17.5, 20, 22.5, 25, 27.5 or about 30 kDa. In some embodiments, the polymer can have a higher $M_w$ (e.g., about 40, 50, 75, or 100 kDa).

In some embodiments, the polymer is provided by preparing a polyacrylamide polymer comprising a plurality of aminoalkyl pendent groups and then reacting a portion of the plurality of aminoalkyl pendent groups with a carboxyarylboronic acid, a carboxyarylboronic acid ester or an activated ester of thereof (e.g., a N-hydroxysuccinimide ester thereof), thereby covalently attaching the arylboronic acid or arylboronic acid ester to some of the side chains via an amide linkage.

In some embodiments, the polyacrylamide polymer comprising the plurality of aminoalkyl pendent groups is first prepared by mono-protecting a diamine and reacting the mono-protected diamine with an acrylic acid or acryloyl halide, such as acryloyl chloride or methacryloyl chloride, to form an acrylamide. The acrylamide can be polymerized (e.g., via free radical polymerization) to form a polyacrylamide comprising protected aminoalkyl side chains, which can be deprotected to from the free amines.

EXAMPLES

The following examples are included to further illustrate various embodiments of the presently disclosed subject matter. However, those of ordinary skill in the art should, in light of the present disclosure, appreciate that many changes can be made in the specific embodiments which are disclosed and still obtain a like or similar result without departing from the spirit and scope of the presently disclosed subject matter.

Example 1

Synthesis of Poly(EDAA-FPBA) and Poly(EDAA-PBA)

Materials:

Ethylenediamine, di-tert-butyl decarbonate ($Boc_2O$), acryloyl chloride, 2, 2'-Azobis(2-methylpropionitrile) (AIBN), tetrahydrofuran (THF), trifluoracetic acid (TFA), dichloromethane ($CH_2Cl_2$), N-hydroxysuccinimide (NHS) and N-(3-dimethylaminopropyl)-N'-ethylcarbodiimide hydrochloride (EDC·HCl) were purchased from Sigma-Aldrich (St. Louis, Missouri, United States of America). 4-Carboxy-3-florobenzeneboronic acid and 4-carboxy-benzeneboronic acid were obtained from Fisher Scientific (Thermo Fisher Scientific, Waltham, Massachusetts, United States of America). All the solvents were treated according to standard purified methods. Unless mentioned otherwise, all the reactions were carried out under $N_2$ atmosphere.

Synthesis: The synthesis of FPBA-modified poly (EDAA)s (i.e., poly(EDAA-FPBA), was performed as shown below in Scheme 1. First, Boc-EDA was prepared by dissolving ethylenediamine (14 mL) in $CHCl_3$ (200 mL) and cooling the solution in an ice bath. $Boc_2O$ (4.1 g) dissolved in $CHCl_3$ (50 mL) was added dropwise in 3 hours, and the reaction was stirred overnight at room temperature. After filtration, the solution was washed with saturated NaCl aqueous solution (3×50 mL), dried over anhydrous $MgSO_4$, filtrated and evaporated to obtain white solid. This solid was used without further purification.

Boc-EDA (1.6 g, 10 mmol) was dissolved in $H_2O$ (50 mL) and filtrated to obtain a clear solution, to which acryloyl chloride (1.5 g, 16 mmol) dissolved in THF (10 mL) was added quickly. $NaHCO_3$ (1.5 g) was then added slowly to the solution, and the reaction was stopped after an additional 30 min. The mixture was extracted using $CH_2Cl_2$ (3×50 mL), dried over anhydrous $MgSO_4$, and filtrated. After evaporation of the solvent, white Boc-EDAA (1.6 g, yield 70%) was obtained. $^1$H-NMR (400 MHz, in $CDCl_3$, δ): 6.54 (s, 1H), 6.22 (d, 1H), 6.1 (q, 1H), 5.6 (d, 1H), 3.4 (q, 2H), 3.3 (s, 2H), 1.42 (s, 9H).

Boc-EDAA (0.5 g) and AIBN (12 mg) were mixed and dissolved in THF (2 mL), which was purged with $N_2$ for 10 min. After incubation at 60° C. overnight, the reaction mixture was diluted with THF (10 mL), added to DI water, and dialyzed against DI water (3×4 L). Finally, the water was lyophilized and white solid was obtained (0.45 g, yield 90%).

Poly(Boc-EDAA) (0.3 g) was dissolved in $CH_2Cl_2$ (10 mL), to which TFA (3 mL) was added and stirred for 2 hours. The solvent was evaporated, and the residual was dialyzed against $H_2O$ (3×4 liters) and lyophilized to obtain poly (EDAA) (0.2 g, yield 90%) as slightly yellow solid.

PBA-NHS was prepared by mixing 4-carboxyphenylboronic acid (2 g, 12 mmol) and N-hydroxysuccinimide (NHS, 2 g, 17 mmol) in DMF (100 mL) and cooling the mixture in an ice bath while stirring. N-(3-dimethylaminopropyl)-N'-ethylcarbodiimide hydrochloride (EDC, 3 g, 18 mmol) was added, and the reaction was stirred overnight at room temperature. The mixture was poured into $CH_2Cl_2$ (200 mL) and washed with HCl (0.1 N, 3×50 mL) and $NaHCO_3$ (0.1 N, 3×50 mL) successively and dried over anhydrous $MgSO_4$. The solvent was evaporated under reduced pressure, and a pure white PBA-NHS was obtained (3 g, yield 90%). $^1$H-NMR (400 MHz, in $CDCl_3$, δ): 8.43 (s, 2H), 8.02 (t, 4H), 2.88 (s, 4H).

FPBA-NHS was prepared by mixing 4-Carboxy-3-fuorophenylboronic acid (2 g, 12 mmol) and N-hydroxysuccinimide (NHS, 2 g, 17 mmol) in DMF (100 mL), which was cooled in an ice bath while stirring. N-(3-dimethylaminopropyl)-N'-ethylcarbodiimide hydrochloride (3 g, 18 mmol) was added, and the reaction was stirred overnight at room temperature. The mixture was poured into $CH_2Cl_2$ (200 mL) and washed with HCl (0.1 N, 3×50 mL) and $NaHCO_3$ (0.1 N, 3×50 mL) successively and dried over anhydrous $MgSO_4$. The solvent was evaporated under reduced pressure, and pure white FPBA-NHS was obtained (2.7 g, yield 80%). $^1$H-NMR (400 MHz, in DMSO-$d_6$, δ): 8.59 (s, 2H), 8.0 (t, 1H), 7.79 (q, 2H), 2.9 (s, 4H).

FPBA modified- and PBA modified-poly(EDAA) were prepared as exemplified by the following synthesis of poly ($EDAA_{0.4}$-$FPBA_{0.6}$). Poly(EDAA) (0.15 g) was dissolved in deionized water (10 mL). FPBA-NHS (220 mg) dissolved in DMSO (2 mL) was added to give a clear solution. Then, solid $NaHCO_3$ was added slowly to maintain the pH around 7.2, and the reaction was stirred for 30 min. Finally, the mixture was dialyzed against deionized water (3×4 L) and subsequently lyophilized to give a white solid (0.3 g, yield 80%).

Scheme 1.
Synthesis of FPBA modified and PBA modified poly(EDAA)s.

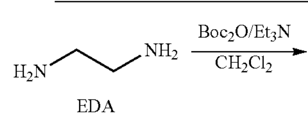

-continued

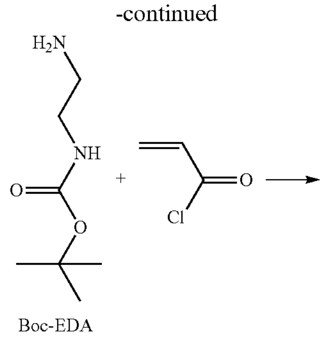

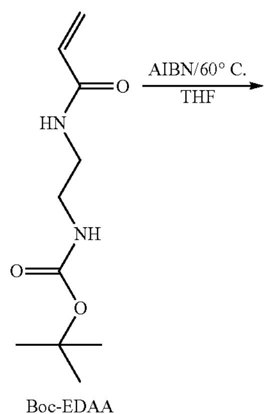

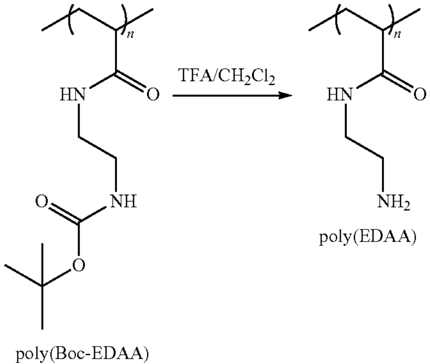

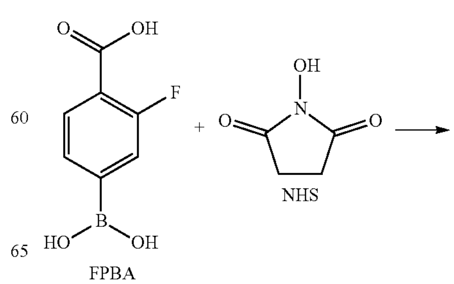

-continued

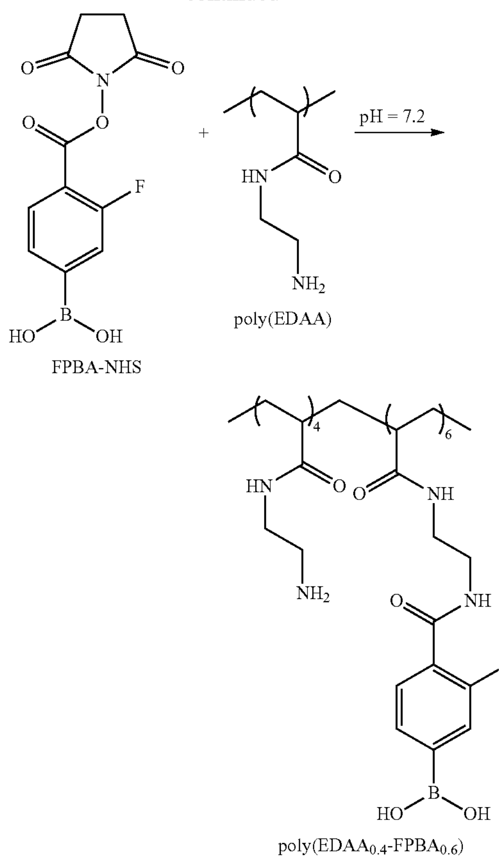

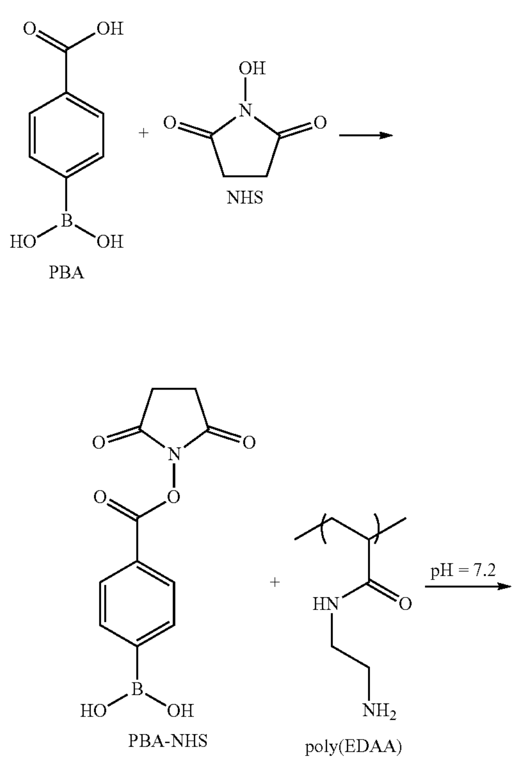

-continued

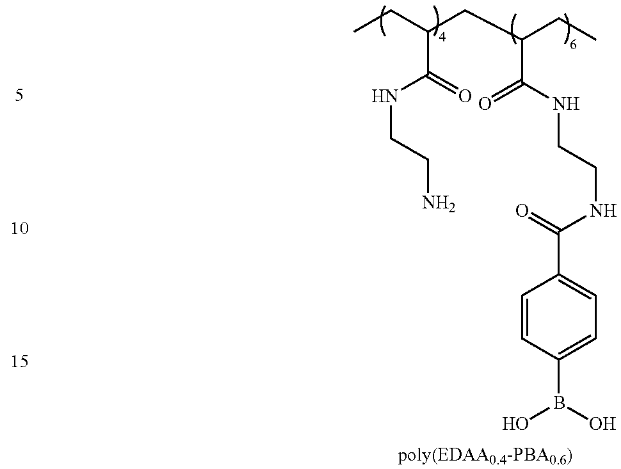

Synthesis Summary:

A polymer with pendant amine groups was synthesized through free radical polymerization of tert-butyl (2-aminoethyl)carbamate (Boc-EDA) and the subsequent deprotection. See Scheme 1. The chemical structures were characterized by $^{1}$H-NMR, while the molecular weight was around 8.7 KDa as measured by gel permeation chromatography. 4-Carboxy-3-fuorophenylboronic acid was activated by NHS and employed to prepare poly($EDAA_{0.4}$-$FPBA_{0.6}$) and poly($EDAA_{0.7}$-$FPBA_{0.3}$). As a comparison, 4-carboxy-phenylboronic acid was also activated and utilized to modify poly(EDAA) and produced poly($EDAA_{0.4}$-$PBA_{0.6}$). After modification, poly($EDAA_{0.7}$-$FPBA_{0.3}$) was soluble in aqueous solution at pH 7.4, while both poly($EDAA_{0.4}$-$FPBA_{0.6}$) and poly($EDAA_{0.4}$-$PBA_{0.6}$) were only dissolved in a slightly acidic aqueous solution.

Example 2

Synthesis of Rhodamine B Labeled Insulin

Rhodamine B isothiocyanate (1 mg) dissolved in DMSO (1 mL) was added to the aqueous solution of insulin (100 mg). $NaHCO_3$ was added to adjust the pH to 8, and the reaction was stirred at room temperature overnight. Then, the mixture was dialyzed against deionized $H_2O$ (3×4 L) and lyophilized to obtain Rhodamine B labeled insulin.

Example 3

Synthesis of Polymer Nanoparticles

Poly($EDAA_{0.4}$-$FPBA_{0.6}$) (1 mg) was dissolved in acidified deionized (DI) $H_2O$ (50 μL). Upon rapid addition of phosphate buffer solution (10 mM, pH=7.4, 1 mL) to this solution, the polymer precipitated and formed stable nanoparticles. Nanoparticle solution from poly($EDAA_{0.4}$-$PBA_{0.6}$) was fabricated by the same method.

Example 4

Synthesis of Insulin Complexes

Complexes were prepared from insulin and poly ($EDAA_{0.4}$-$FPBA_{0.6}$) with various ratios. The preparation of poly($EDAA_{0.4}$-$FPBA_{0.6}$)/insulin complex is described as an example of the synthesis of polymer/insulin complexes of the presently disclosed subject matter. Both insulin (1 mg) and poly($EDAA_{0.4}$-$FPBA_{0.6}$) (1 mg) were respectively dissolved in acidified $H_2O$ (50 μL) and mixed. NaOH (0.1 N) was added carefully, and the pH was finely tuned to 7.4 until a white precipitate formed due to the electrostatic interaction between insulin and polymer, indicating the formation of polymer/insulin complexes. To this suspension, PBS (1 mL) was added, and the solution was centrifuged, and the solid was further washed for several times with PBS. Finally, the suspension was kept in PBS at pH=7.4 and used directly for in vitro and in vivo experiment.

The complex precipitation was highly stable, suggesting a strong interaction between insulin and polymer. Without being bound to any one theory, the water insolubility of poly($EDAA_{0.4}$-$FPBA_{0.6}$) is proposed to be critical for stabilizing the complex formed between polymer and insulin.

Example 5

Glucose Adsorption and Nanoparticle Characterization

Nanoparticle Characterization:

The size and ζ-potential of nanoparticles were measured on a Zetasizer (Malvern Panalytical, Malvern, United Kingdom). The impact of glucose concentration on the ζ-potential of nanoparticles was determined by adding, various amounts of glucose to the solution of nanoparticles, which were allowed to stand for 2 min before taking the measurement. Of note, nanoparticles of poly($EDAA_{0.4}$-$FPBA_{0.6}$) would precipitate when glucose was added to 400 mg/mL, and rapid ascertainment of this measurement was critical.

Glucose Adsorption:

Insulin complexes, composed of insulin (1 mg) and polymer (1 mg), were suspended in PBS 7.4 (1 mL) and were allocated to centrifuge tubes, to which glucose was added to acquire different glucose solution (100 or 400 mg/dL). This solution was incubated at 37° C. and the glucose concentration was monitored by a Clarity GL2Plus glucose meter (Clarity Diagnostics, Boca Raton, Florida, United States of America). The concentration was calibrated using a standard curve.

Figure 2A:
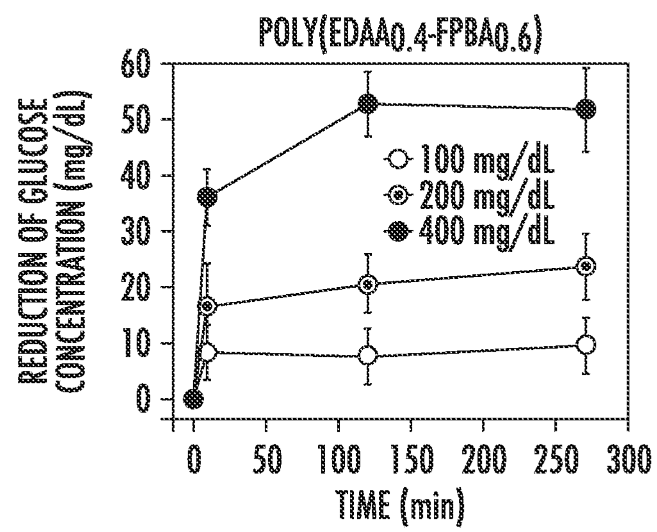
FIG. 2A is a graph showing the glucose binding ability of F-insulin, i.e., a polymer-insulin complex comprising an equal weight of insulin and polymer, where the polymer is poly(ethylene diamine acrylamide) (poly(EDAA)) wherein 60 percent of the pendent amino groups are grafted to fluorophenyl boronic acid (FPBA) groups (i.e., poly($EDAA_{0.4}$-$FPBA_{0.6}$). The F-insulin was incubated in a 100 (unfilled circles), 200 (half-filled circles), or 400 (filled circles) milligrams per deciliter (mg/dL) glucose solution and glucose binding ability was assessed by measuring the reduction of the glucose concentration (in mg/dL). Error bars represent the standard deviation (S.D.) of three independent experiments (n=3).
Figure 2B:
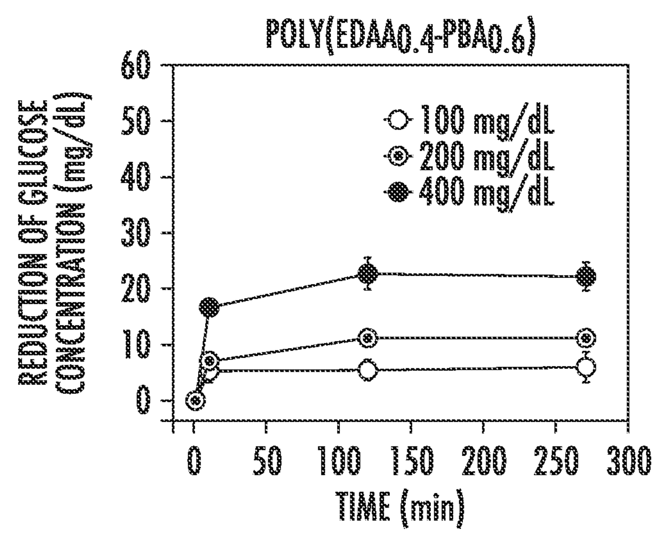
FIG. 2B is a graph showing the glucose binding ability of B-insulin, i.e., a polymer-insulin complex comprising an equal weight of insulin and polymer, where the polymer is poly(ethylene diamine acrylamide) (poly(EDAA)) where 60 percent of the pendent amino groups are grafted to phenyl boronic acid (PBA) groups (i.e., poly($EDAA_{0.4}$-$PBA_{0.6}$). The B-insulin was incubated in a 100 (unfilled circles), 200 (half-filled circles), or 400 (filled circles) milligrams per deciliter (mg/dL) glucose solution and glucose binding ability was assessed by measuring the reduction of the glucose concentration (in mg/dL). Error bars represent the standard deviation (S.D.) of three independent experiments (n=3).
Figure 2C:
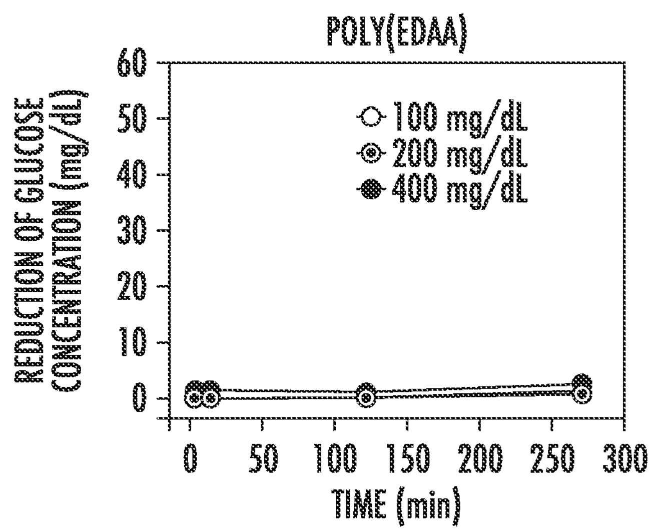
FIG. 2C is a graph showing the glucose binding ability of N-insulin, i.e., a polymer-insulin complex comprising an equal weight of insulin and polymer, where the polymer is poly(ethylene diamine acrylamide) (poly(EDAA)). The N-insulin was incubated in a 100 (unfilled circles), 200 (half-filled circles), or 400 (filled circles) milligram per deciliter (mg/dL) glucose solution and glucose binding ability was assessed by measuring a reduction of the glucose concentration (in mg/dL). Error bars represent the standard deviation (S.D.) of three independent experiments (n=3).

Summary:

The glucose-binding ability of polymers was evaluated in PBS at pH 7.4 with varied glucose concentrations of 0, 100 (a typical normoglycemic level), 200, and 400 mg/dL (a typical hyperglycemic level). Polymer-insulin complexes comprised of an equal weight of insulin and polymer, namely poly($EDAA_{0.4}$-$FPBA_{0.6}$) complexed insulin (F-insulin), poly($EDAA_{0.4}$-$PBA_{0.6}$) complexed insulin (B-insulin), and poly(EDAA) complexed insulin (N-insulin), were prepared. Glucose concentrations in were calibrated in PBS solution by a standard curve. After the addition of glucose to an F-insulin solution, the concentration of glucose decreased by and 30 mg/dL for the 100 and 400 mg/dL glucose solutions, respectively, within 10 min. See FIG. 2A. Surprisingly, further adsorption of glucose by F-insulin was observed in 400 mg/dL glucose solution, such that a total decrease of 50 mg/dL of the glucose concentration was observed within 120 minutes, indicating that more than 90% of the FPBA moieties were bound to glucose, which, without being bound to any one theory is ascribed to the enhanced diol-capturing ability arising from adjacent amine groups. See Ren et al., Angew. Chem. Int. Edit., 2009, 48, 6704-6707; and Lianq and Liu, Chem. Commun., 2011, 47, 2255-2257. Much lower glucose binding was observed for the solutions of B-insulin (see FIG. 2B), while negligible glucose binding was observed for the solutions of N-insulin. See FIG. 2C.

Figure 2D:
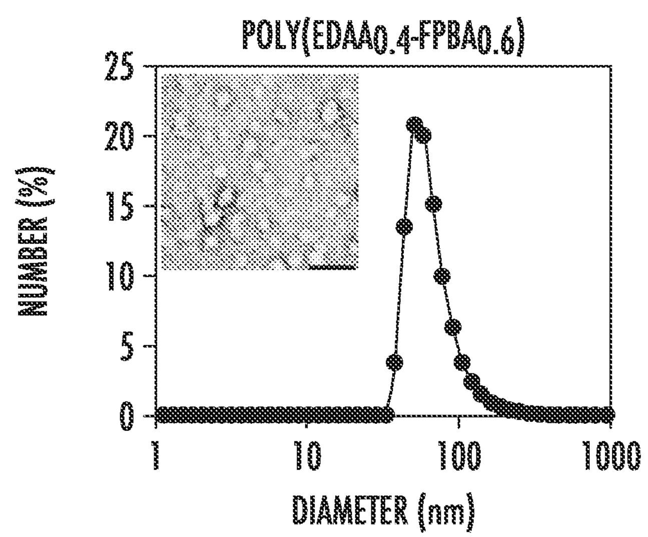
FIG. 2D is a graph showing the hydrodynamic size distribution (number of particles (percentage (%)) versus diameter (in nanometers (nm)) determined by dynamic light scattering (DLS)) of nanoparticles prepared from poly(ethylene diamine acrylamide) (poly(EDAA)) where 60 percent of the pendent amino groups are grafted to fluorophenyl boronic acid (FPBA) groups (i.e., poly($EDAA_{0.4}$-$FPBA_{0.6}$). The inset shows a representative transmission electron microscope (TEM) image of the nanoparticles. The black scale bar in the lower right of the TEM image represents 100 nm.
Figure 2E:
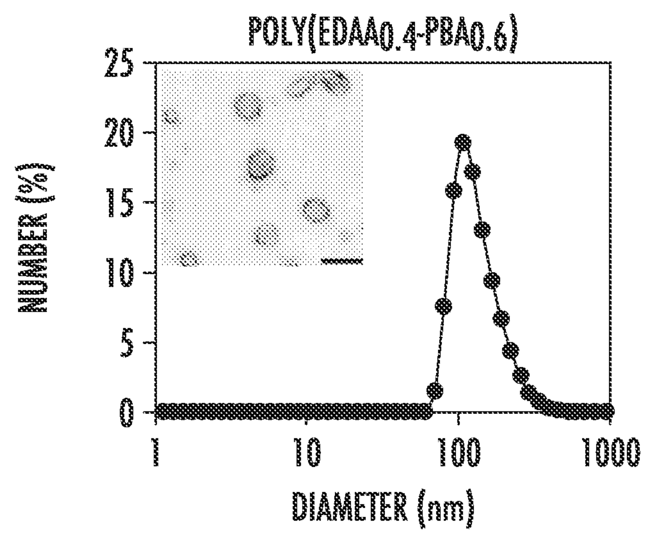
FIG. 2E is a graph showing the hydrodynamic size distribution (number of particles (percentage (%)) versus diameter (in nanometers (nm)) determined by dynamic light scattering (DLS)) of nanoparticles prepared from poly(ethylene diamine acrylamide) (poly(EDAA)) where 60 percent of the pendent amino groups are grafted to phenyl boronic acid (PBA) groups (i.e., poly($EDAA_{0.4}$-$PBA_{0.6}$). The inset shows a representative transmission electron microscope (TEM) image of the nanoparticles. The black scale bar in the lower right of the TEM image represents 100 nm.
Figure 2F:
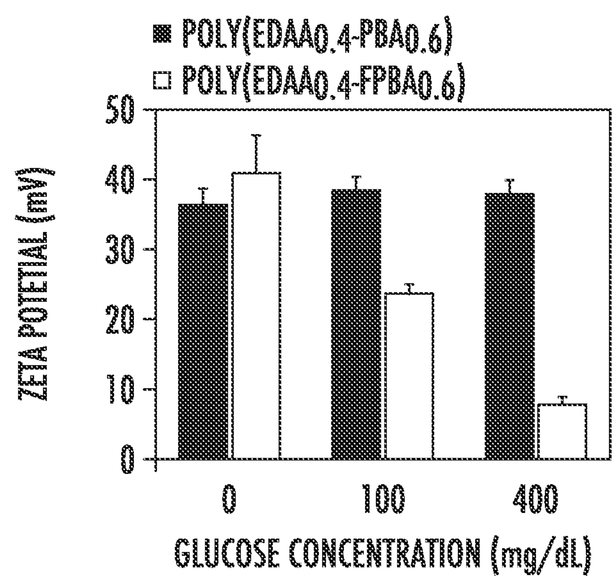
FIG. 2F is a graph of the glucose-dependent zeta (ζ)-potentials of nanoparticles prepared from poly(ethylene diamine acrylamide) (poly(EDAA)) where 60 percent of the pendent amino groups are grafted to fluorophenyl boronic acid (FPBA) groups (i.e., poly($EDAA_{0.4}$-$FPBA_{0.6}$; unfilled bars) and poly(ethylene diamine acrylamide) (poly(EDAA)) where 60 percent of the pendent amino groups are grafted to phenyl boronic acid (PBA) groups (i.e., poly($EDAA_{0.4}$-$PBA_{0.6}$; filled bars). Zeta potential (in millivolts) is measured at three different glucose concentrations (0 milligrams/ deciliter (mg/dL), 100 mg/dL, and 400 mg/dL). Error bars represent the standard deviation (S.D.) of three independent experiments (n=3).

To determine whether glucose binding could lead to the reduction of positive charge on polymers, polymeric nanoparticles were prepared by dripping a concentrated acidic aqueous solution of poly($EDAA_{0.4}$-$FPBA_{0.6}$) or poly ($EDAA_{0.4}$-$PBA_{0.6}$) into PBS at pH 7.4. Both Poly ($EDAA_{0.4}$-$FPBA_{0.6}$) and poly($EDAA_{0.4}$-$PBA_{0.6}$) formed stable spherical nanoparticles as measured by dynamic light scattering (DLS) and transmission electron microscopy (TEM) See FIGS. 2D and 2E. As shown in FIG. 2F, the original ζ-potential of poly($EDAA_{0.4}$-$FPBA_{0.6}$) nanoparticles was +40 mV in the absence of glucose, which gradually decreased to +22 mV in 100 mg/dL glucose solution and further decreased to +8 mV in 400 mg/dL glucose solution. During this process, the pH of the solution was maintained at 7.4, suggesting that the change of ζ-potential resulted from glucose-binding of the FPBA moiety, rather than a pH change. The particles began to aggregate about 5 min after the glucose concentration reached 400 mg/dL. Without being bound to any one theory, this observation is believed to be due to weakened electrostatic repulsion between nanoparticles. In contrast, the ζ-potential of poly($EDAA_{0.4}$-$PBA_{0.6}$) nanoparticles was maintained at a nearly constant level.

Example 6

In Vitro Insulin Release

Insulin Release Measurement Method:

Briefly, insulin (1 mg) loaded in complexes with different polymers with different ratios were allocated to centrifuge tubes containing PBS (pH=7.4, 1 mL) and various amounts of glucose were added to prepare different concentrations (0, 100, 200, 400 mg/dL). Then, the centrifuge tubes were incubated at 37° C. and vibrated. At timed intervals, an aqueous solution (50 μL) was collected and centrifuged to obtain the supernatant solution (20 μL), which was stained with Coomassie blue (200 μL) and the absorbance at 595 nm was measured on a multimode plate reader (Tecan Group Ltd., Männedorf, Switzerland). The insulin concentration was calibrated by a standard curve.

Results:

The insulin release from the complexes upon glucose variation was assessed. The insulin release kinetics can be tuned by varying the weight ratios of poly($EDAA_{0.4}$-$FPBA_{0.6}$) to insulin. See FIGS. 3A-3D. For all complexes, the insulin release rate was significantly faster in 400 mg/dL glucose solution than in 0, 100 or 200 mg/dL glucose solutions. Moreover, the complex prepared from an equal weight of insulin and poly($EDAA_{0.4}$-$FPBA_{0.6}$) (F-insulin) showed the most efficacious glucose-dependent insulin release dynamic, where more than 80% of insulin was released in three hours under 400 mg/dL glucose, about two-fold higher insulin release than that in 100 mg/dL glucose. See FIG. 3D. In contrast, the insulin release from N-insulin and B-insulin was relatively slow. As a control, a poly($EDAA_{0.4}$-$FPBA_{0.6}$) suspension without insulin was also treated with 400 mg/dL glucose solution; however, no absorbance was observed for the supernatant after it was mixed with Coomassie blue, eliminating concerns regarding potential interference from poly($EDAA_{0.4}$-$FPBA_{0.6}$) in the insulin measurement. To further validate glucose-responsive insulin release, insulin was labeled with Rhodamine B (RhB-insulin) and complexed with poly($EDAA_{0.4}$-

$FPBA_{0.6}$). Significantly enhanced insulin release was demonstrated from the F-insulin under a hyperglycemic state (see FIG. 3E) in contrast to the slow insulin release from control groups.

Moreover, the insulin release rate from the complexes in glucose solution was steadily increased when the glucose concentration was gradually increased (from 0 to 400 mg/dL), where a maximum of 4-fold enhancement in insulin release rate was achieved, indicating the ultrafast glucose-response rate of F-insulin. See FIG. 3F. This fast kinetics upon glucose variation has the potential to effectively regulate BGLs in real-time. Additionally, a pulsatile release profile for insulin was achieved over several cycles of incubating complexes in a glucose solution with an alternating glucose concentration between 100 and 400 mg/dL. See FIG. 3G. Of note, the time interval was set to 2 min based on the fast response rate of F-insulin. Meanwhile, the far-UV circular dichroism (CD) spectra of native insulin and released insulin from the complex at the same concentration (0.5 mg/mL) were compared and found to be similar, indicating that the released insulin retained α-helical secondary structure and bioactivity.

Example 7

In Vivo Studies in Mouse Model of Diabetes

Glucose Control Studies of Complexes Using Streptozotocin (STZ)-Induced Diabetic Mice:

Diabetic mice were allocated to different groups (n=5) and treated with subcutaneously injected free insulin or insulin loaded in complexes (i.e., F-insulin; equal weight poly($EDAA_{0.4}$-$FPBA_{0.6}$) and insulin) at various doses (30 or 80 IU/kg); or complex (F-insulin) together with PF-127 gel at a dose of 300 IU/kg. The blood glucose levels were monitored by a Clarity GL2Plus glucose meter (Clarity Diagnostics, Boca Raton, Florida, United States of America). The study was continued until the blood glucose levels were stabilized. PF-127 was used at a concentration of 50% in aqueous solution, and the complex was suspended in the gel. Before injection, the gel was kept at 4° C. for higher fluidity to facilitate subcutaneous injection. The blood insulin levels were measured by collecting 50 μL of blood, and the plasma was isolated and stored at −20° C. until measurement using a human insulin ELISA kit according to the manufacturer's protocol (Invitrogen, Carlsbad, California, United States of America).

Inflammation Assessment:

The inflammation caused by subcutaneous injection of the PF-127 gel was measured as a proxy for biocompatibility. After removal of back hair, diabetic mice were subcutaneously injected with PF-127 (100 μL) loaded with insulin complex (F-insulin; 300 IU/kg). On day 3 or 7 post-injection, mice were anesthetized, and pieces of skins from the treated site were collected and fixed in 4% formaldehyde and processed using hematoxylin and eosin (H&E) staining. Images were taken using a microscope (Olympus Corporation, Tokyo, Japan).

Plasma Insulin Level Measurement:

The plasma insulin level in vivo was monitored by collecting 50 μL of blood from the tail vein of the mice at timed intervals. The plasma was isolated and stored at −20° C. until assay. The plasma insulin concentration was measured using Human Insulin ELISA kit (Invitrogen, Carlsbad, California, United States of America) according to the manufacturer's protocol.

Statistical Analysis:

Differences in blood glucose levels between treated groups and control groups were calculated using unpaired student's t-test. The difference was considered as significant when the two-tailed P-values was smaller than 0.05.

Results:

The in vivo therapeutic efficacy of insulin-polymer complex was evaluated in a type 1 diabetic mouse model induced by STZ. The diabetic mice were assigned to four groups treated with one of F-insulin, B-insulin, or native insulin at a dose of 80 IU/kg or with PBS as a control. The BGLs of all treated groups decreased to below 200 mg/dL, indicating the retention of activity of complexed insulin. See FIG. 4A. Moreover, F-insulin was shown to maintain BGLs within the normal range (<200 mg/dL) for more than 8 hours, much longer than the three hours associated with free insulin and B-insulin. Also, negligible hypoglycemia was observed in mice treated with F-insulin.

Next, the superior release rate of insulin under hyperglycemic conditions by the F-insulin complex was further evaluated. A spike of blood insulin level of 7500 μIU/mL was observed at around 30 min post-injection of F-insulin, consistent with the rapid down-regulation of BGLs. The blood insulin level quickly decreased to 750 μIU/mL at 1.5 h and further decreased to 22 μIU/mL at 4 h post-treatment, which is sufficient for maintaining normoglycemia while avoiding hypoglycemia. By comparison, the blood insulin level of mice treated by B-insulin showed a flank peak of insulin level at 30 min post-injection, which is believed to be mainly due to the burst release of loosely-adsorbed insulin. However, the fast elimination of insulin from blood circulation (see Cresto et al., Acta Physiol. Lat. Am., 1977, 27, 7-15) and slow insulin release from B-insulin failed to maintain a basal level of plasma insulin.

Intraperitoneal glucose tolerance tests (IPGTT) associated with in vivo glucose response were performed at three hours post-treatment of F-insulin at an insulin dose of 80 IU/kg. Blood glucose peaks were observed for all groups after intraperitoneal glucose injection (see FIG. 4B), while the healthy mice and F-insulin treated mice re-established normoglycemia in a brief period. IPGTT was also carried out at four hours post-treatment with F-insulin, where a spike in BGLs was observed. See FIG. 4C. Remarkably, the blood insulin level increased quickly from 30 μIU/mL to 250 μIU/mL over time (see FIG. 4C), and then gradually decreased to 39 μIU/mL. Such rapid glucose-responsive insulin release kinetics are useful for maintaining normoglycemia in the face of glucose challenge.

To further demonstrate the potential of glucose-sensitive F-insulin in regulating BGLs for a long term, insulin complexes were subcutaneously co-injected with an in-situ formed absorbable gel (PLURONIC™ F-127 gel (BASF Corporation, Florham Park, New Jersey, United States of America, PF-127). Similar experimental groups were set but with an increased insulin dose (300 IU/kg). All insulin complexes showed a regulating effect on BGLs; with F-insulin being found to regulate blood glucose within a normal range, which was lasted for more than 30 hours. See FIG. 4D. Meanwhile, the BGLs of mice treated by gel loaded with B-insulin decreased slowly in the initial period after administration and was maintained in a mild-hyperglycemic state during entire experiment process. These results validated the importance of glucose responsiveness in both the fast-release insulin at the initial state and the slow-release at the normoglycemia period. Further, Hematoxylin and Eosin (H&E) staining results indicated that slight neutrophil infiltration was observed on day 3 post-administration of F-insulin loaded PF-127 gel, but was healed by day 7.

In summary, a subcutaneously injectable glucose-responsive insulin-polymer complex with ultrafast insulin release kinetics has been developed, based on a charge switch-driven mechanism. This complex, made through a simple and high loading-efficiency process, was stable in PBS at pH 7.4 without glucose, and released basal insulin under a normal glucose level, while instantly released insulin under a hyperglycemic state. In vivo fast glucose-responsive insulin release was demonstrated after intraparietal glucose injection. Additionally, sustained long-term regulation of BGLs can be achieved by co-injection of a gel matrix. Moreover, this method provides a broad platform for bio-responsive drug delivery that can respond to specific physiological cues with fast kinetics.

Example 8

In Vivo Studies in Minipig Model of Diabetes

Glucose Control Studies of Complexes Using Streptozotocin-Induced Diabetic Minipigs:

Göttingen minipigs (6-month old) were injected with streptozotocin (STZ, 150 mg/kg) to establish the diabetic minipig model. Three diabetic pigs were treated with subcutaneously injected free insulin (1 IU/kg) and three diabetic pigs were treated subcutaneously with complexed insulin (i.e., equal weight poly($EDAA_{0.4}$-$FPBA_{0.6}$) to insulin, F-insulin) at a dose of 1 IU/kg. All pigs had undergone overnight fasting prior to treatment. Two meals are provided normally during the treatment. The blood glucose levels in all six pigs were continuously monitored using continuous glucose monitoring (Dexcom G4® continuous glucose monitor; Dexcom, San Diego, California, United States of America).

Oral Glucose Tolerance Tests on Diabetic Pigs:

Three diabetic pigs were treated with subcutaneously-injected free insulin or complex (i.e., F-insulin) at two doses (1 IU/kg) after an overnight fasting, then glucose (0.5 g/kg) was given four hours post-treatment. The blood glucose levels were continuously monitored using continuous glucose monitoring (Dexcom G4® continuous glucose monitor; Dexcom, San Diego, California, United States of America).

Results:

Similar to the results obtained in diabetic mice, F-insulin showed a prolonged BGL regulating effect in type 1 diabetic pigs as compared with free insulin. See FIG. 5A. In addition, oral glucose tolerance tests were carried out at an insulin dose of 1 IU/kg. When pigs were treated with complex at an insulin-equivalent dose of 1 IU/kg, a glucose spike appeared for all challenged groups within two hours and no difference was observed between complex and insulin treated groups. See FIG. 5B. However, a subsequent afternoon meal (2 hours post-oral administration of glucose) led to a sharp increase in BGLs of the pigs treated with free insulin, while only a relative slower increase in BGLs was observed for minipigs treated with complex.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A composition comprising:

(a) a positively-charged polymer, wherein the positively-charge, polymer has a polyacrylamide backbone comprising a plurality of side chains comprising an ammonium group and a plurality of side chains comprising a glucose-binding group, wherein the glucose-binding croup is a halophenylboronic acid group; and (b) insulin or a bioactive derivative thereof.

2. The composition of claim 1, wherein the halophenylboronic acid group is a fluorophenylboronic acid group.

3. The composition of claim 1, wherein the polymer has a structure of formula (I):

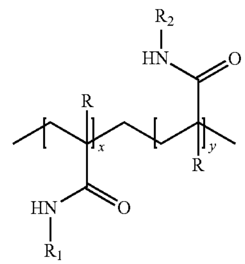

wherein x and y are each integers greater than 1, wherein the sum of integers x and y is at least about 10; and wherein the ratio of x to y is between about 7:3 and about 1:5;

R is H or alkyl;

$R_1$ is a protonated aminoalkyl group; and $R_2$ is a group comprising a halophenylboronic acid.

4. The composition of claim 3, wherein $R_1$ has the structure $-L-NH_3^+$, wherein L is a $C_1$-$C_6$ straight or branched, substituted or unsubstituted alkylene group.

5. The composition of claim 3, wherein $R_2$ has the structure $-L_1-NH-C(=O)-R_3$, wherein $L_1$ is a $C_1$-$C_6$ straight or branched, substituted or unsubstituted alkylene group and wherein $R_3$ is a fluorophenylboronic acid group or other halophenylboronic acid group.

6. The composition of claim 3, wherein the ratio of x to y is about 2:3.

7. The composition of claim 1, wherein the composition comprises a weight ratio of positively-charged polymer (a) to insulin or bioactive derivative thereof (b) of between about 2:1 and about 1:4.

8. The composition of claim 7, wherein the weight ratio of (a) to (b) is about 1:1.

9. A nanoparticle or microparticle comprising the composition of claim 1.

10. The nanoparticle or microparticle of claim 9, wherein the nanoparticle or microparticle has a diameter of between about 0.1 micrometers (μm) and about 1000 μm.

11. A microneedle array comprising the nanoparticle or microparticle of claim 9, wherein said microneedle array comprises a plurality of microneedles, wherein each of said plurality of microneedles has a length of between about 20 and about 1000 micrometers.

12. A skin patch comprising the microneedle array of claim 11.

13. A pharmaceutical formulation comprising a pharmaceutically acceptable carrier and a composition of claim 1.

14. A method of delivering insulin or a bioactive derivative thereof to a subject in need thereof, the method comprising administering a skin patch of claim 12.

15. The method of claim 14, wherein the subject is a mammal.

16. The method of claim 14, wherein the subject has Type 1 or Type 2 diabetes.

17. The method of claim 14, wherein the skin patch or pharmaceutical formulation releases insulin at a rate that corresponds directly to blood glucose levels of the subject.

18. A method of treating diabetes in a subject in need thereof, wherein the method comprises administering a skin patch of claim 12 to the subject.

19. The method of claim 18, wherein the administration is performed once a day.

20. A pharmaceutical formulation comprising a pharmaceutically acceptable carrier and a nanoparticle or microparticle of claim 9.

21. A method of delivering insulin or a bioactive derivative thereof to a subject in need thereof, the method comprising administering a pharmaceutical formulation of claim 13 to the subject.

22. A method of treating diabetes in a subject in need thereof, wherein the method comprises administering a pharmaceutical formulation of claim 13 to the subject.

23. The composition of claim 1, wherein the insulin or bioactive derivative thereof is recombinant human insulin.

24. The composition of claim 3, wherein R is $C_1$-$C_6$ alkyl.

25. The composition of claim 4, wherein L is —$CH_2CH_2$—.

26. The composition of claim 5, wherein $L_1$ is —$CH_2CH_2$—.

27. The nanoparticle or microparticle of claim 10, wherein the nanoparticle or microparticle has a diameter of about 50 μm.

28. The microneedle array of claim 11, wherein each of the plurality of microneedles has a length of about 600 micrometers.

29. The skin patch of claim 12, wherein said skin patch comprises one or more backing layers and/or skin compatible adhesives.

30. The method of claim 15, wherein the subject is a human.

* * * * *